(12) United States Patent
Aharoni et al.

(10) Patent No.: US 8,088,161 B2
(45) Date of Patent: Jan. 3, 2012

(54) COMPRESSED HAPTICS

(75) Inventors: Eli Aharoni, Tel Aviv (IL); Yossi Gross, Moshav Mazor (IL); Gideon Dotan, Yehud (IL); Iden Avihar, Raanana (IL)

(73) Assignee: Visioncare Ophthalmic Technologies Inc., Saratoga, CA (US)

( * ) Notice: Subject to any disclaimer, the term of this patent is extended or adjusted under 35 U.S.C. 154(b) by 1923 days.

(21) Appl. No.: 11/193,781

(22) Filed: Jul. 28, 2005

(65) Prior Publication Data

US 2007/0027538 A1 Feb. 1, 2007

(51) Int. Cl.
*A61F 2/16* (2006.01)
(52) U.S. Cl. ............... 623/6.41; 623/6.38; 623/6.43
(58) Field of Classification Search .............. 623/6.4, 623/6.5, 6.12, 6.38, 6.52–6.64
See application file for complete search history.

(56) References Cited

U.S. PATENT DOCUMENTS

| | | | |
|---|---|---|---|
| 4,056,855 A * | 11/1977 | Kelman | 623/6.38 |
| 4,074,368 A | 2/1978 | Levy, Jr. et al. | |
| 4,172,297 A | 10/1979 | Schlegel et al. | |
| 4,373,218 A | 2/1983 | Schchar | |
| 4,463,458 A | 8/1984 | Seidner | |
| 4,527,294 A | 7/1985 | Heslin | |
| 4,581,031 A | 4/1986 | Koziol et al. | |
| 4,596,578 A | 6/1986 | Kelman | |
| 4,666,446 A | 5/1987 | Koziol et al. | |
| 4,687,484 A | 8/1987 | Kaplan | |
| 4,710,197 A | 12/1987 | Donn et al. | |
| 4,731,078 A | 3/1988 | Stoy et al. | |
| 4,743,254 A | 5/1988 | Davenport | |
| 4,759,761 A | 7/1988 | Portnoy | |
| 4,816,030 A | 3/1989 | Robinson | |
| 4,833,890 A * | 5/1989 | Kelman | 623/6.17 |
| 4,892,543 A | 1/1990 | Turley | |
| 4,911,714 A | 3/1990 | Poley | |
| 4,911,715 A | 3/1990 | Kelman | |
| 4,968,127 A | 11/1990 | Russell et al. | |
| 4,976,732 A | 12/1990 | Vorosmarthy | |
| 4,994,082 A | 2/1991 | Richards et al. | |
| 5,026,396 A | 6/1991 | Darin | |
| 5,108,429 A | 4/1992 | Wiley | |
| 5,222,981 A | 6/1993 | Werblin | |
| 5,354,335 A | 10/1994 | Lipshitz et al. | |
| 5,384,606 A | 1/1995 | Koch et al. | |
| 5,391,202 A | 2/1995 | Gross et al. | |
| 5,405,387 A | 4/1995 | Sodero et al. | |
| 5,628,798 A | 5/1997 | Eggleston et al. | |
| 5,653,751 A | 8/1997 | Samiy et al. | |

(Continued)

FOREIGN PATENT DOCUMENTS

DE 34 28 895 A1 2/1986

(Continued)

OTHER PUBLICATIONS

An Office Action dated Jan. 13, 2009, which issued during the prosecution of Applicant's U.S. Appl. No. 11/420,327.

(Continued)

*Primary Examiner* — David Isabella
*Assistant Examiner* — Joshua Levine
(74) *Attorney, Agent, or Firm* — Fish & Richardson P.C.

(57) ABSTRACT

An injectable intraocular implant including an optics portion and a resilient, flexible haptics portion mounted coaxially with the optics portion and a method for inserting the implant into the eye.

6 Claims, 22 Drawing Sheets

U.S. PATENT DOCUMENTS

| | | | |
|---|---|---|---|
| 5,769,889 A | 6/1998 | Kelman | |
| 5,769,890 A | 6/1998 | McDonald | |
| 5,814,103 A | 9/1998 | Lipshitz et al. | |
| 5,876,442 A | 3/1999 | Gross et al. | |
| 5,928,283 A | 7/1999 | Gross et al. | |
| 5,964,802 A | 10/1999 | Anello et al. | |
| 6,007,579 A * | 12/1999 | Lipshitz et al. | 623/6.11 |
| 6,066,171 A | 5/2000 | Lipshitz et al. | |
| 6,197,057 B1 | 3/2001 | Peyman et al. | |
| 6,342,073 B1 * | 1/2002 | Cumming et al. | 623/6.46 |
| 6,464,725 B2 | 10/2002 | Skotton | |
| 6,569,199 B1 | 5/2003 | Dotan | |
| 6,596,026 B1 | 7/2003 | Gross et al. | |
| 6,849,090 B2 | 2/2005 | Nigam | |
| 6,902,577 B2 | 6/2005 | Lipshitz et al. | |
| 6,913,620 B2 | 7/2005 | Lipshitz et al. | |
| 7,008,448 B2 | 3/2006 | Lipshitz et al. | |
| 7,276,080 B2 | 10/2007 | Murakami et al. | |
| 2002/0143395 A1 | 10/2002 | Skottun | |
| 2002/0173846 A1 | 11/2002 | Blake et al. | |
| 2003/0060881 A1 | 3/2003 | Glick et al. | |
| 2003/0078656 A1 | 4/2003 | Nguyen | |
| 2003/0105522 A1 | 6/2003 | Glazier | |
| 2003/0109926 A1 | 6/2003 | Portney | |
| 2003/0187502 A1 | 10/2003 | Lipshitz | |
| 2003/0187503 A1 | 10/2003 | Lipshitz et al. | |
| 2004/0148022 A1 | 7/2004 | Eggleston | |
| 2004/0181279 A1 | 9/2004 | Nun | |
| 2005/0071002 A1 | 3/2005 | Glazier | |

FOREIGN PATENT DOCUMENTS

| | | |
|---|---|---|
| DE | 44 03 326 C1 | 6/1995 |
| DE | 195 01 444 A1 | 7/1996 |
| EP | 0162573 | 11/1985 |
| EP | 0 212 616 A2 | 3/1987 |
| EP | 0 419 740 A1 | 4/1991 |
| EP | 0 897 702 A2 | 2/1999 |
| EP | 1 092 402 B1 | 4/2001 |
| EP | 1475055 | 11/2004 |
| FR | 2666735 | 3/1992 |
| GB | 1303579 | 1/1973 |
| GB | 2 181 355 A | 4/1987 |
| WO | WO-83/01566 A1 | 5/1983 |
| WO | WO-94/07435 A1 | 4/1994 |
| WO | WO-0004849 | 2/2000 |
| WO | WO-00/38593 A1 | 7/2000 |

OTHER PUBLICATIONS

An Office Action dated Jan. 20, 2009, which issued during the prosecution of Applicant's Japanese Patent Application No. 2004-7118.

An International Search Report dated Feb. 26, 2007, which issued during the prosecution of Applicant's PCT Patent Application No. PCT/IL06/00873.

* cited by examiner

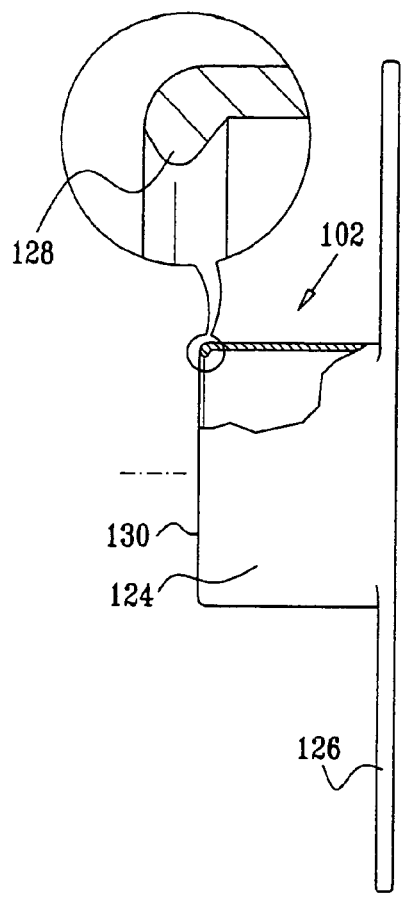
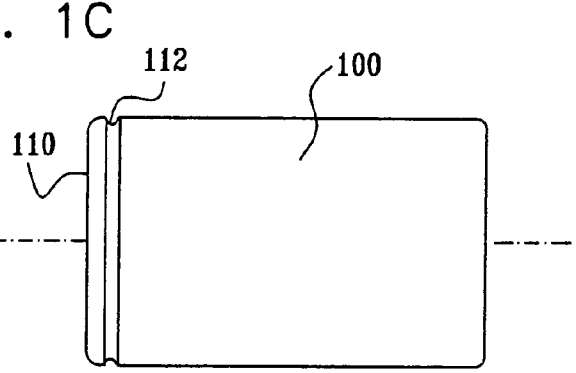
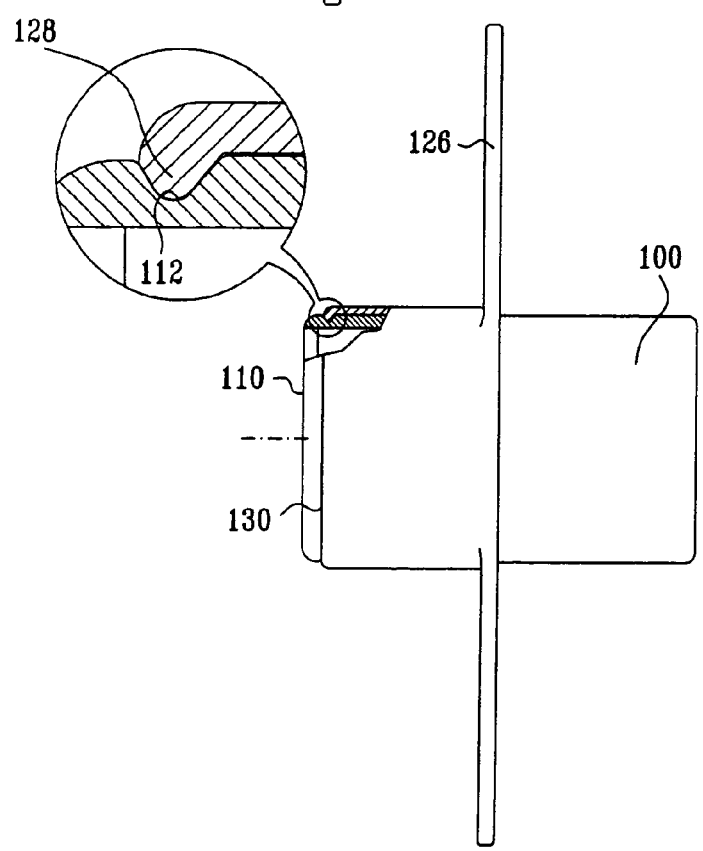
FIG. 1C
FIG. 1D

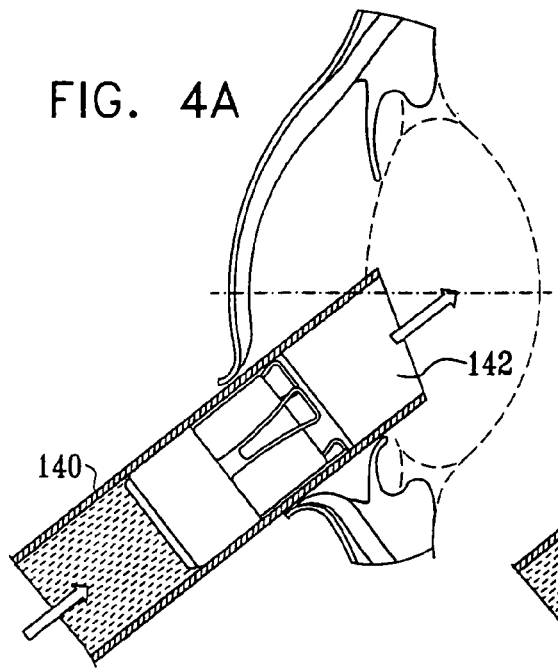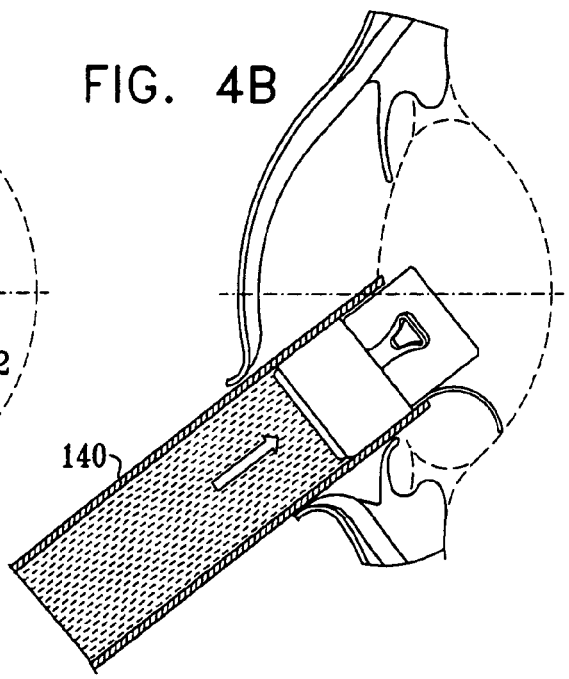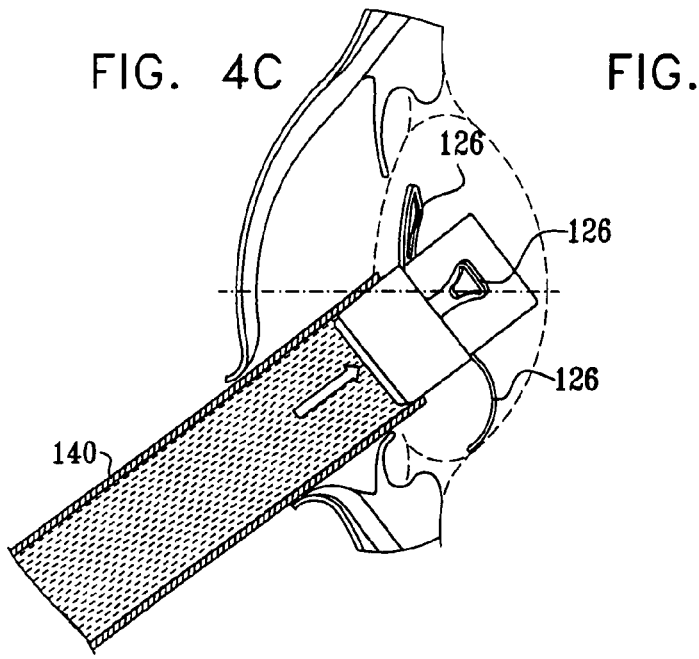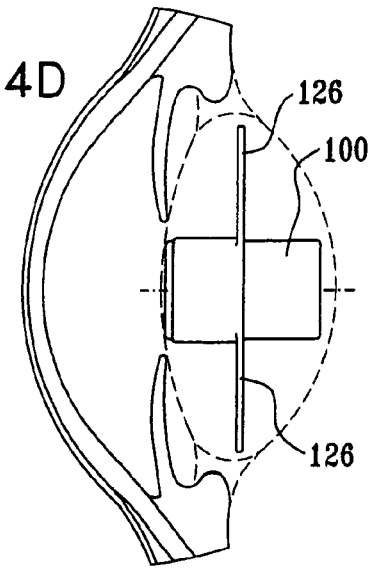

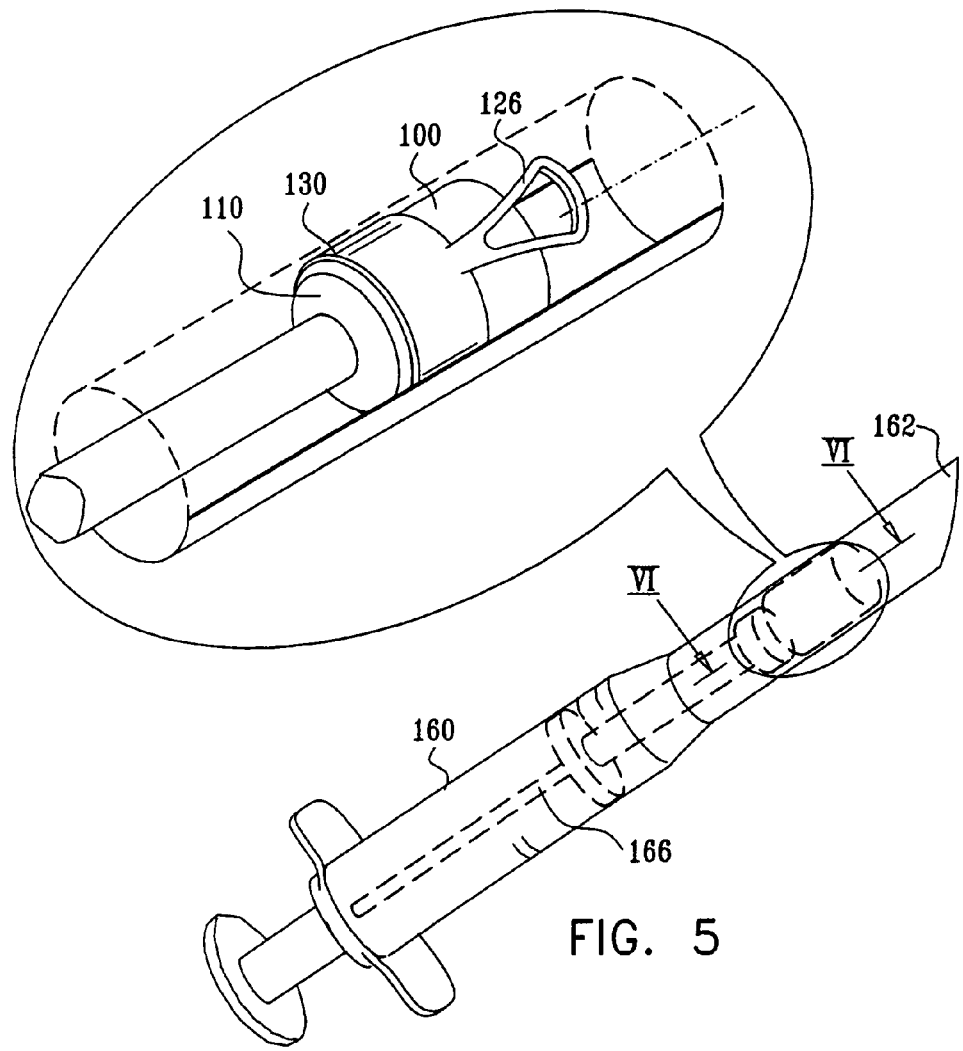
FIG. 5
FIG. 6
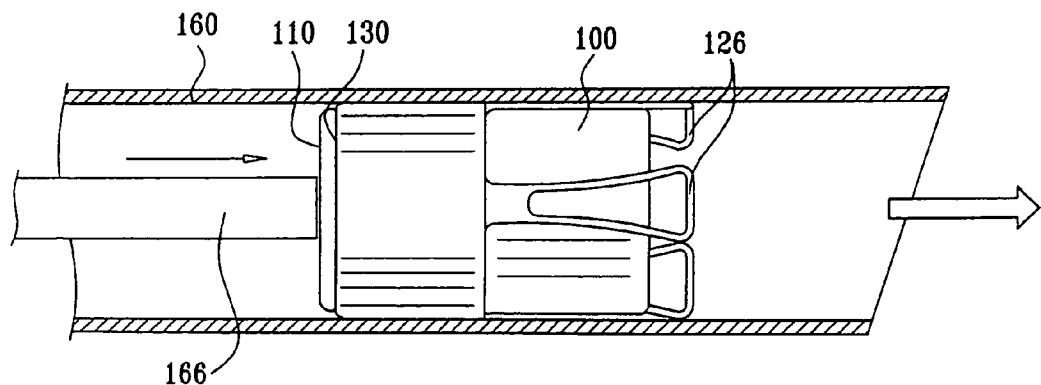

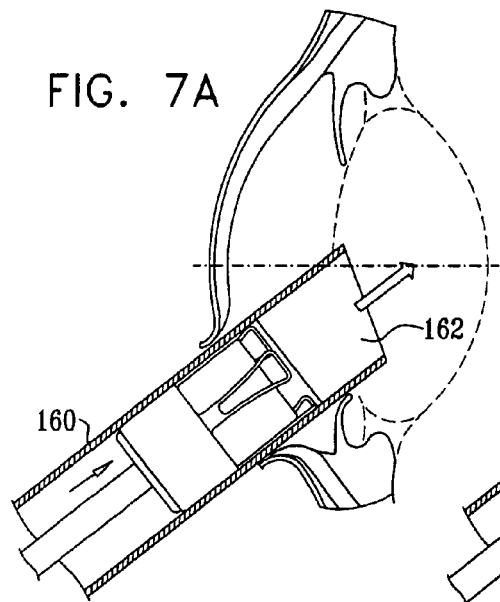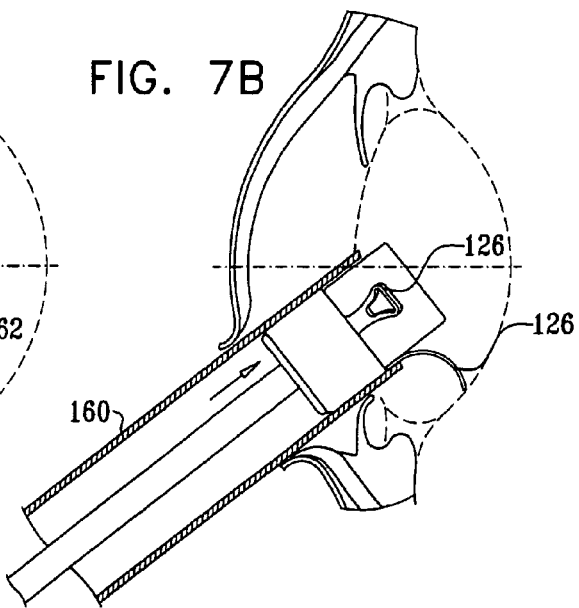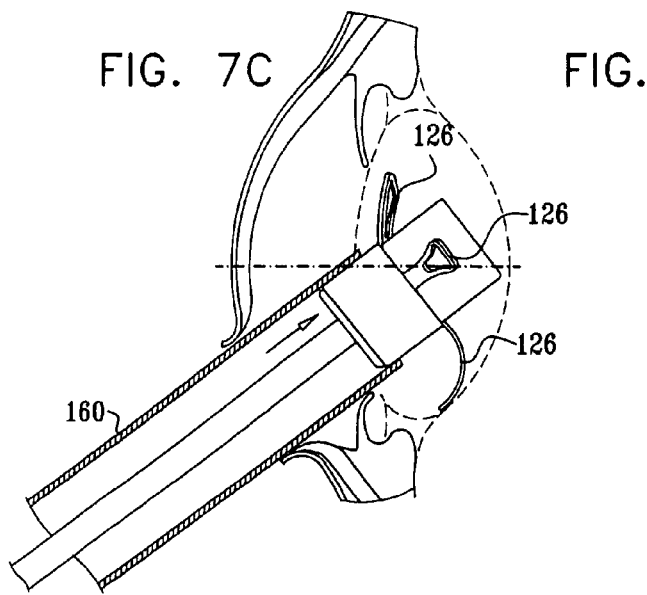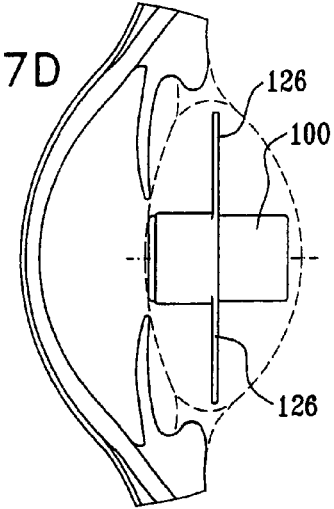

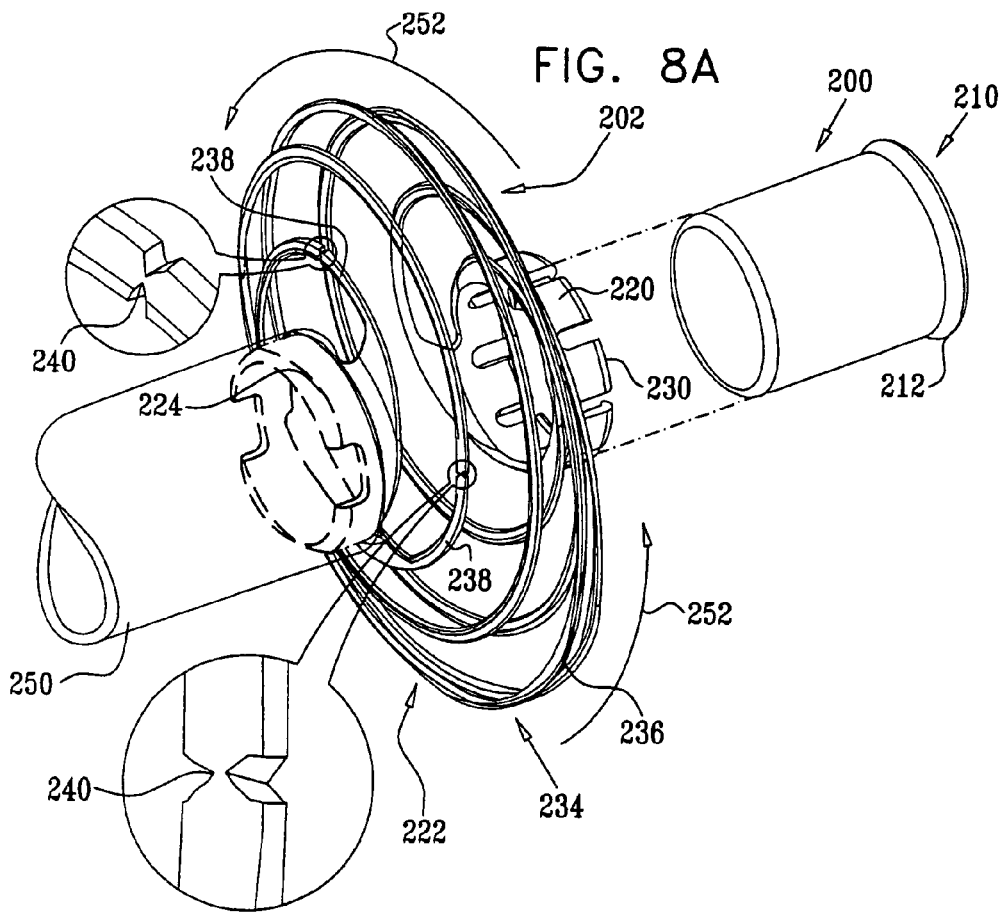
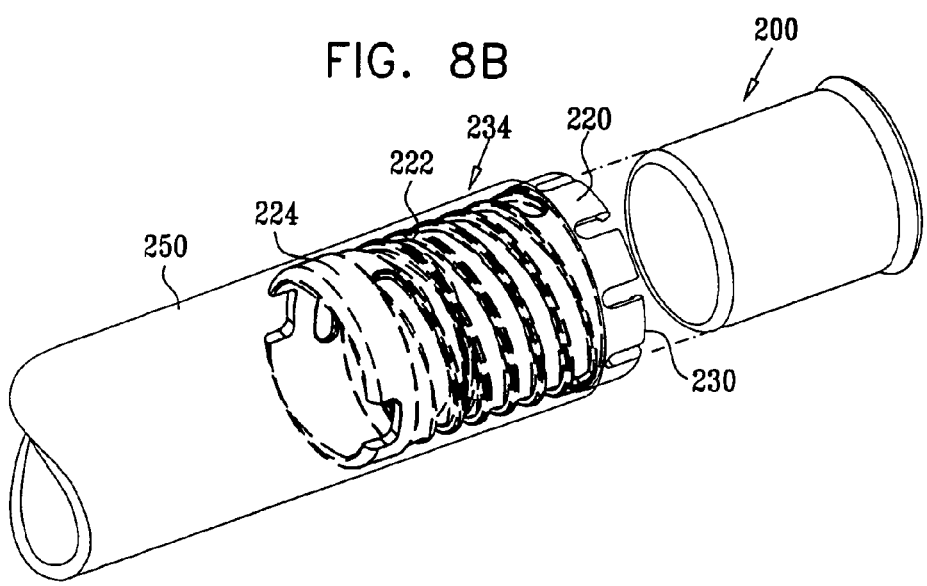

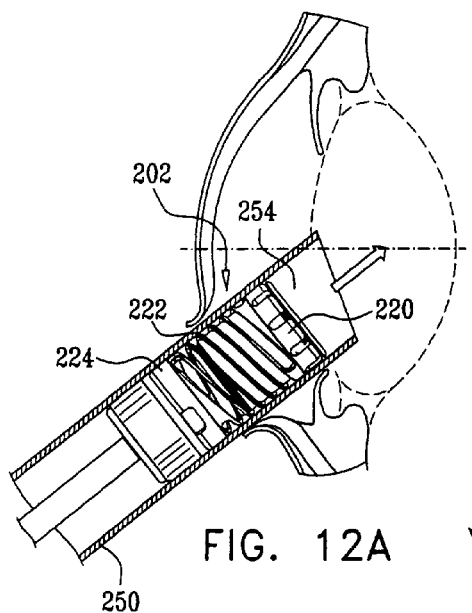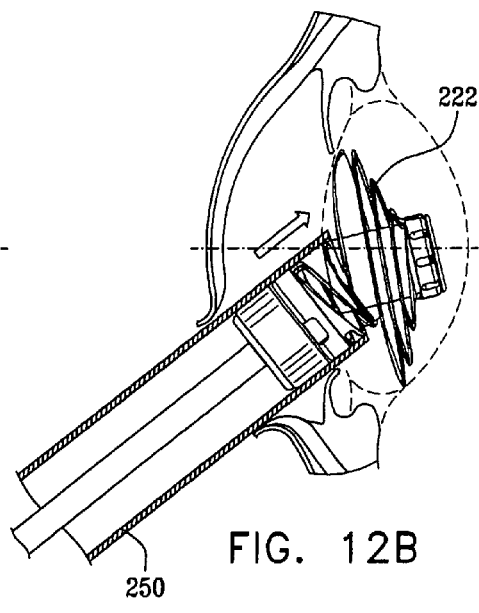
FIG. 12A  FIG. 12B
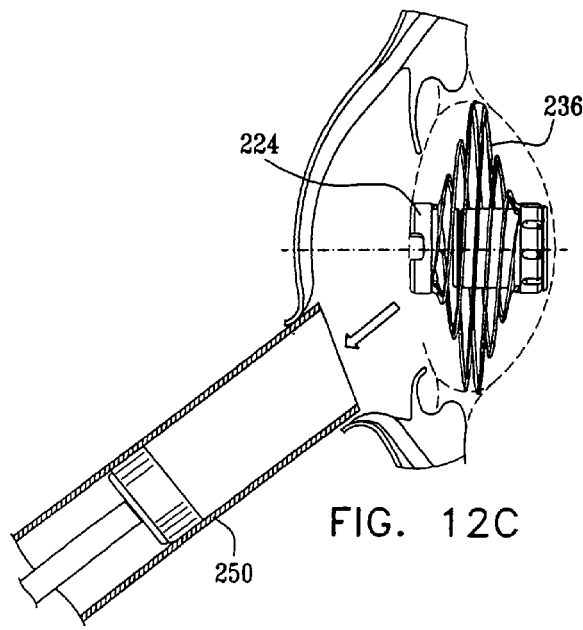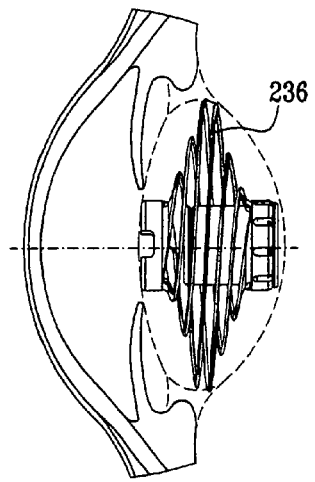
FIG. 12C  FIG. 12D

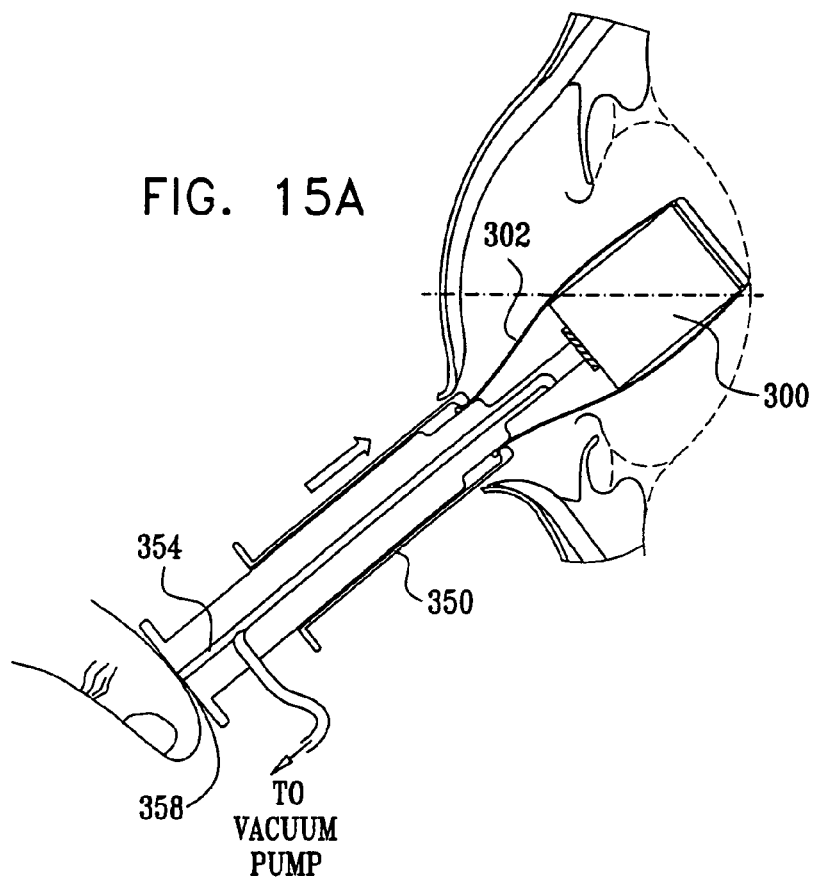
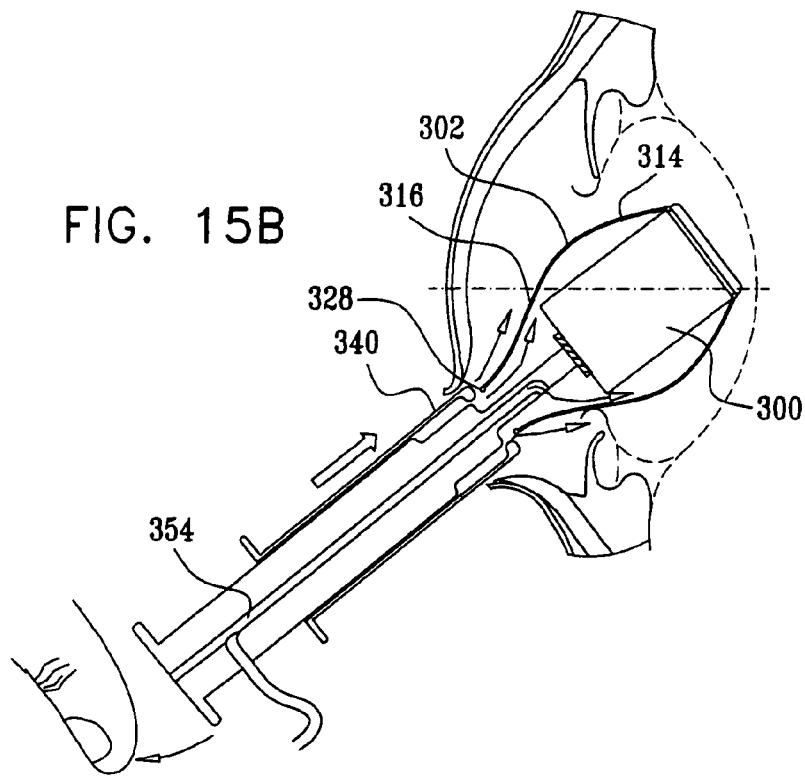

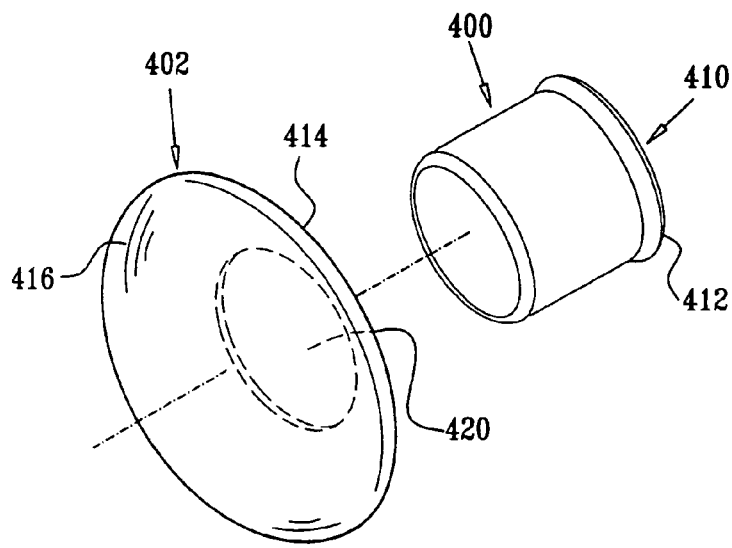
FIG. 16A
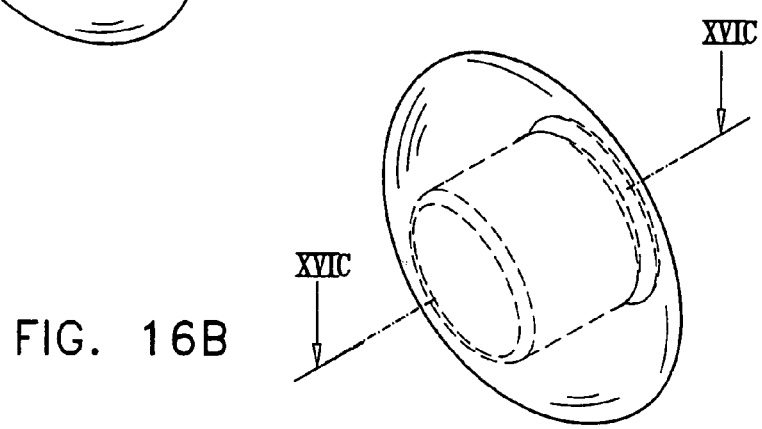
FIG. 16B
FIG. 16C
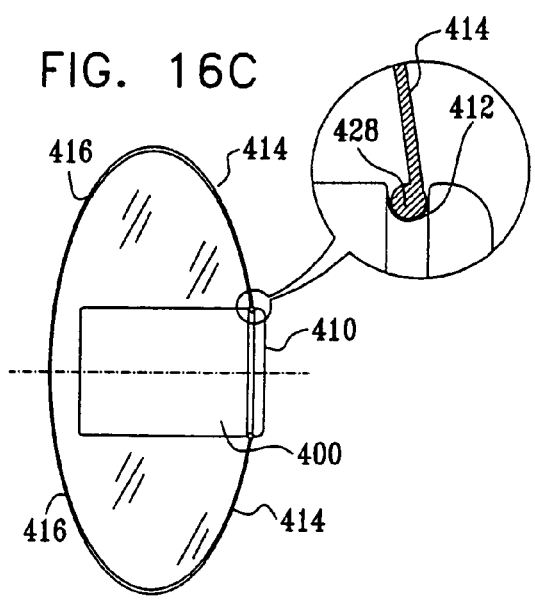

US 8,088,161 B2

COMPRESSED HAPTICS

REFERENCE TO CO-PENDING APPLICATIONS

Applicants hereby make reference to the following co-pending U.S. Patent Applications, the disclosures of which are hereby incorporated by reference:

U.S. Ser. No. 10/321,793, filed Dec. 17, 2002, entitled "Intraocular Implants"; U.S. Ser. No. 10/342,160, filed Jan. 14, 2003, entitled "Intraocular Lens Implant" and U.S. Ser. No. 10/489,388, filed Mar. 11, 2004, entitled "Intraocular Implants."

FIELD OF THE INVENTION

The present invention relates to ocular implants generally and more particularly to intraocular implants.

BACKGROUND OF THE INVENTION

The following patent publications are believed to represent the current state of the art:

U.S. Pat. Nos. 5,814,103; 5,876,442; 5,928,283; 6,007,579; 6,066,171; 5,653,751; 6,596,026; 6,464,725; 5,391,202; 5,384,606; 4,074,368; 4,994,082; 5,628,798; 5,222,981; 4,172,297; 5,769,890; 4,892,543; 4,373,218; 4,968,127; 4,759,761; 4,976,732 and 5,769,889;

Published U.S. Application 2001/018,612;

Published PCT Applications WO 94/07,435; WO 00/38593 and WO 83/01566;

Foreign Patent Publications DE 4,403,326; EP 1,092,402; EP 0,419,740; GB 2,181,355; EP 0,897,702; EP 0,212,616; DE 3,428,895 and DE 19,501,444.

SUMMARY OF THE INVENTION

The present invention seeks to provide an improved intraocular implant.

There is thus provided in accordance with a preferred embodiment of the present invention an injectable intraocular implant including an optics portion and a resilient, flexible haptics portion mounted coaxially with the optics portion.

Preferably, the optics portion and the haptics portion are arranged for mutual snap fit engagement.

Preferably, the optics portion includes a telescope. Additionally or alternatively, the haptics portion is formed of biocompatible plastic.

Preferably, the haptics portion includes a cylindrical portion having integrally formed therewith a plurality of outwardly extending haptics wings.

Preferably, the haptics portion includes an outwardly extending helical portion including at least one helical section. Additionally, each of the at least one helical section includes a haptics spiral portion, a residual spiral portion and a frangible portion connecting the haptics spiral portion and the residual spiral portion.

Alternatively, the haptics portion includes a hollow, generally cylindrical structure defining a generally circular inward facing wall portion and a generally circular outward facing wall portion. Additionally, the inward facing wall portion defines a generally circular optics engagement aperture therein. Alternatively, the inward facing wall portion and the outward facing wall portion each define a generally circular optics engagement aperture therein.

There is also provided in accordance with anther preferred embodiment of the present invention a method for inserting an intraocular implant into an eye including providing an injectable intraocular implant including an optics portion and a resilient, flexible haptics portion mounted coaxially with the optics portion, locating the injectable intraocular implant in a delivery tube of a syringe, inserting the delivery tube of a syringe into a lens capsule of an eye and injecting the injectable intraocular implant into the lens capsule.

Preferably, the injecting includes utilizing fluid pressure to force the implant into the lens capsule. Additionally, the fluid is biocompatible fluid.

Preferably, the haptics include haptics wings and the locating includes folding the haptics wings over the optics portion.

Preferably, the locating includes arranging the implant with an outward facing end of the optics portion arranged rearward in the delivery tube.

Alternatively, the haptics portion includes an outwardly extending helical portion and the locating includes winding the helical portion into a coil. Additionally, the injecting includes rotating the syringe.

Preferably, the outwardly extending helical portion includes a haptics spiral portion, a residual spiral portion and a frangible portion connecting the haptics spiral portion and the residual spiral portion and the rotating causes the frangible portion to break, thereby separating the haptics spiral portion from the residual spiral portion.

Alternatively, the haptics portion includes an outward facing wall portion and the locating includes pulling the outward facing wall portion over an outward facing end of the optics portion. Additionally, the locating includes sealing a fluid flow passageway in the syringe. Additionally, the injecting includes unsealing the fluid flow passageway.

Preferably, the locating includes drawing the haptics portion into a delivery syringe.

Preferably, the method also includes puncturing the haptics portion.

BRIEF DESCRIPTION OF THE DRAWINGS

The present invention will be understood and appreciated more fully from the following detailed description, taken in conjunction with the drawings in which:

FIGS. 1C and 1D are simplified respective exploded and assembled side view illustrations of the injectable intraocular implant of FIGS. 1A & 1B;

FIGS. 4A, 4B, 4C and 4D are simplified sectional illustrations of four stages of the injection of the intraocular implant of FIGS. 1A-1D in the delivery syringe arrangement of FIGS. 2 & 3 into the eye of a patient;

FIGS. 5 and 6 are simplified pictorial and sectional illustrations of the injectable intraocular implant of FIGS. 1A-1D located in a specially designed, non fluid-filled hypodermic delivery syringe;

FIGS. 7A, 7B, 7C and 7D are simplified sectional illustrations of four stages of the injection of the intraocular implant of FIGS. 1A-1D in the delivery syringe arrangement of FIGS. 5 & 6 into the eye of a patient;

FIGS. 8A and 8B are simplified respective exploded and assembled pictorial illustrations of an injectable intraocular implant constructed and operative in accordance with another preferred embodiment of the present invention;

FIGS. 12A, 12B, 12C and 12D are simplified sectional illustrations of four stages of the injection of the intraocular implant of FIGS. 8A-8D in the delivery syringe arrangement of FIGS. 9 & 10 into the eye of a patient in accordance with another preferred embodiment of the present invention;

FIGS. 15A, 15B, 15C and 15D are simplified sectional illustrations of four stages of the injection of the intraocular implant of FIGS. 13A-13C in the delivery syringe arrangement of FIGS. 14A & 14B into the eye of a patient;

FIGS. 16A and 16B are simplified respective exploded and assembled pictorial illustrations of an injectable intraocular implant constructed and operative in accordance with still another preferred embodiment of the present invention;

FIG. 16C is a simplified assembled side view illustration of the injectable intraocular implant of FIGS. 16A & 16B;

DETAILED DESCRIPTION OF PREFERRED EMBODIMENTS

Figure 1A:
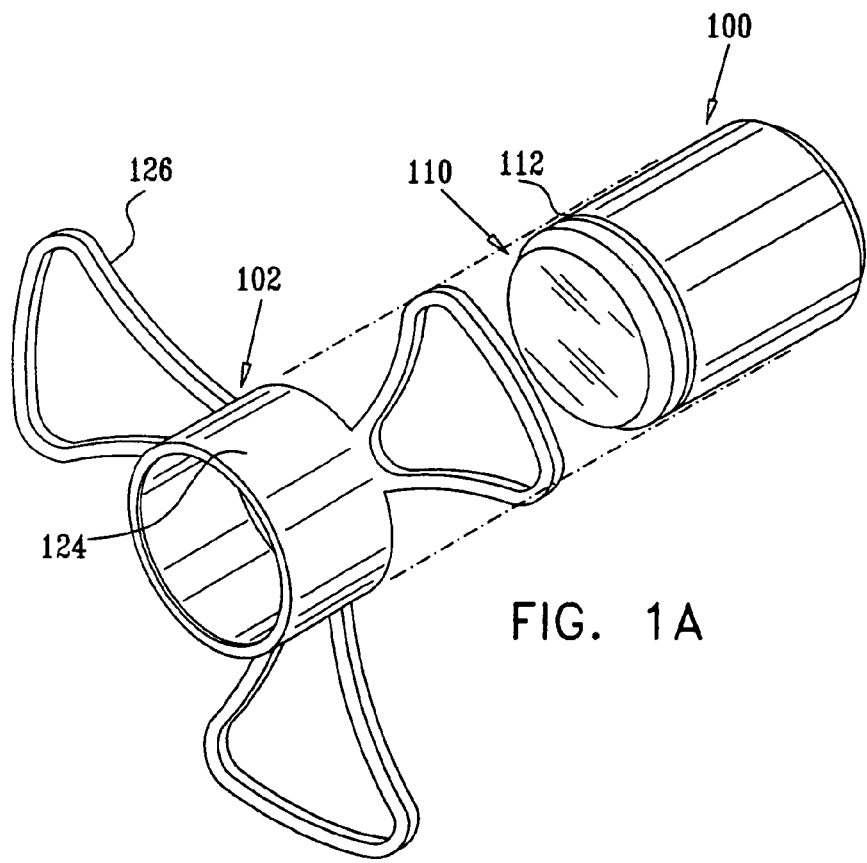
FIGS. 1A and 1B are simplified respective exploded and assembled pictorial illustrations of an injectable intraocular implant constructed and operative in accordance with a preferred embodiment of the present invention.
Figure 1B:
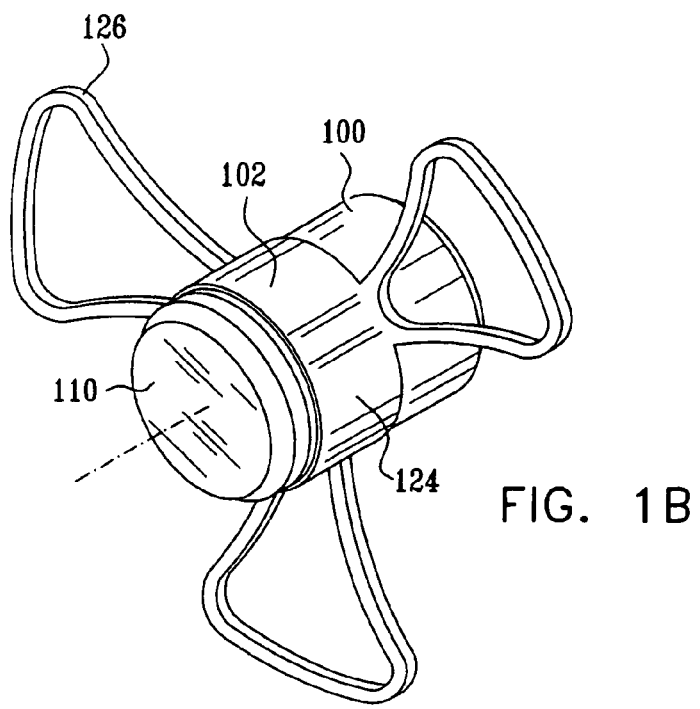

Reference is now made to FIGS. 1A-1D, which illustrate an injectable intraocular implant constructed and operative in accordance with a preferred embodiment of the present invention. It is seen that the implant preferably includes an optics portion 100 and a haptics portion 102 which is preferably snap-fitted onto the optics portion 100.

The optics portion 100 may be any suitable optics portion and is preferably, but not necessarily, a telescope. Preferred intraocular implants are described in applicants/assignee's published patent documents listed hereinbelow, the disclosures of which are hereby incorporated by reference:

U.S. Pat. Nos. 5,391,202; 5,354,335; 5,814,103; 5,876,442; 5,928,283; 6,007,579; 6,066,171; 6,569,199 and 6,596,026, and U.S. published applications U.S. Ser. Nos. 10/342,160 and 10/321,793.

The optics portion 100 may incorporate any one or more of the features described in the abovementioned patent documents in any suitable combination and is preferably in the form of a cylinder having adjacent one end thereof, hereinafter referred to as the outward facing end 110, a peripheral groove 112. The haptics portion 102 is preferably formed of a resilient, flexible material, such as biocompatible plastic, and includes a cylindrical portion 124 having integrally formed therewith a plurality of outwardly extending haptics wings 126. Cylindrical portion 124 is preferably formed with an inwardly directed peripheral protrusion 128 adjacent one end thereof, hereinafter referred to as the outward facing end 130. Protrusion 128 is arranged for normally non-removable snap-fit engagement with groove 112 on optics portion 100, when cylindrical portion 124 is in coaxial surrounding relationship with optics portion 100 as shown.

It is appreciated that the peripheral groove 112 of the optics portion 100 may be located at any suitable location therealong and the inwardly directed peripheral protrusion 128 of cylindrical portion 124 of haptics portion 102 may be located at any suitable location therealong to provide normally non-removable snap-fit engagement of optics portion 100 and haptics portion 102.

Figure 2:
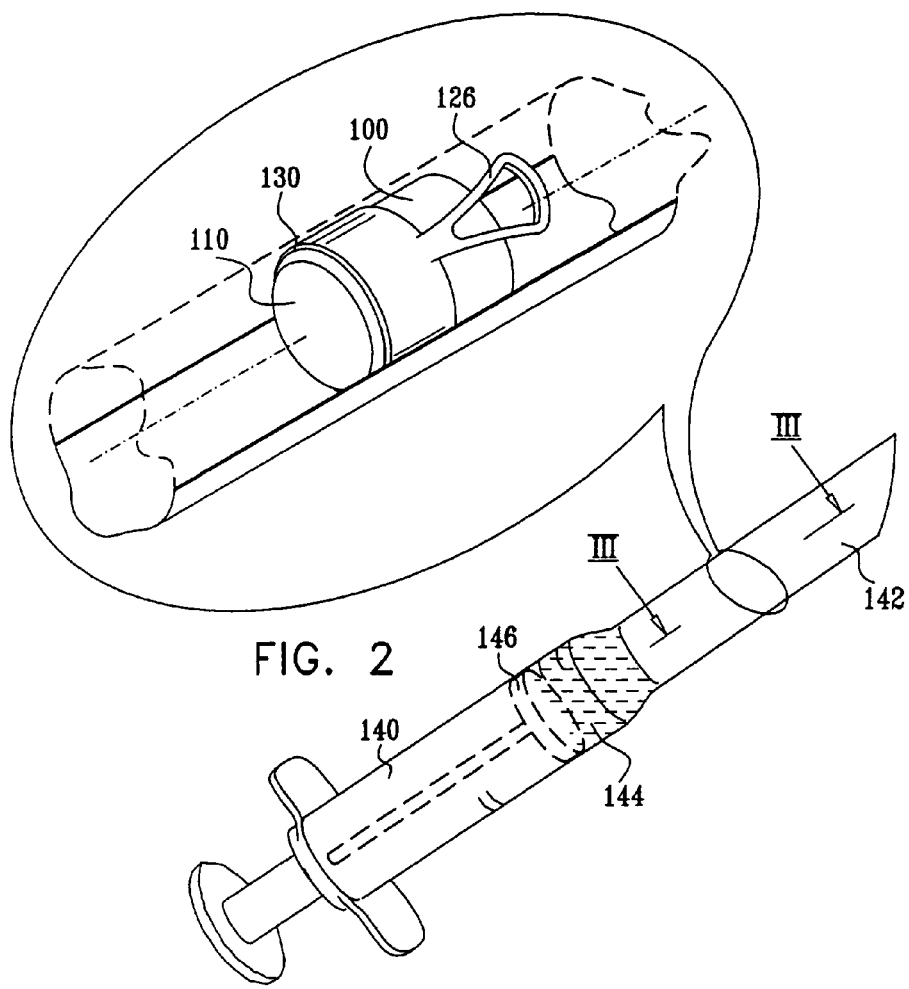
FIGS. 2 and 3 are simplified pictorial and sectional illustrations of the injectable intraocular implant of FIGS. 1A-1D located in a fluid-filled hypodermic delivery syringe.
Figure 3:
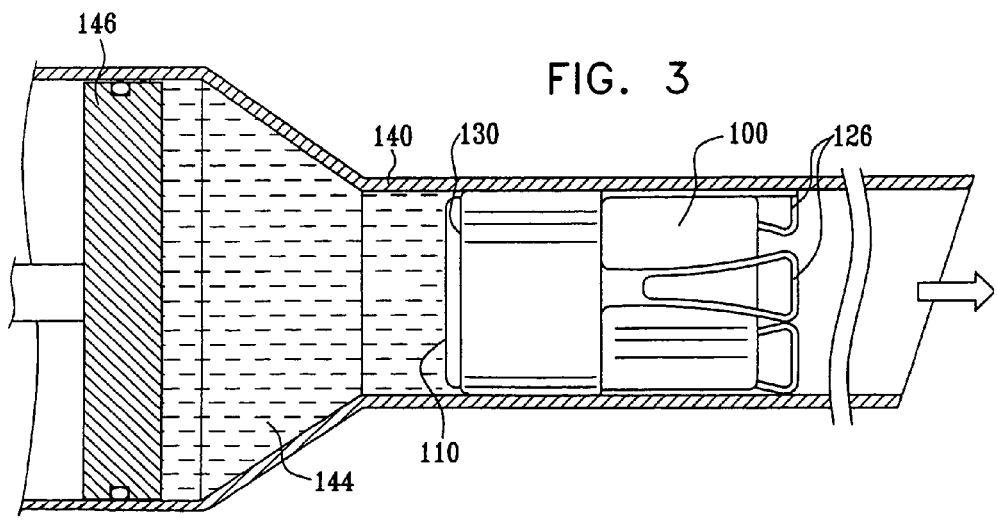

Reference is now made to FIGS. 2 and 3, which are simplified pictorial and sectional illustrations of the injectable intraocular implant of FIGS. 1A-1D located in a fluid-filled hypodermic delivery syringe 140. It is seen that haptics wings 126 are folded over the optics portion 100 and that the implant is arranged with outward facing ends 110 and 130 arranged rearward in a delivery tube 142 of delivery syringe 140. Fluid, such as biocompatible fluid 144, is located forward of a piston 146 of delivery syringe 140 and rearward of the implant.

Reference is now made to FIGS. 4A, 4B, 4C and 4D, which are simplified sectional illustrations of four stages of the injection of the intraocular implant of FIGS. 1A-1D in the delivery syringe arrangement of FIGS. 2 & 3 into the eye of a patient. FIG. 4A shows initial insertion of the tip of the delivery tube 142 of delivery syringe 140 into the lens capsule of the eye. FIG. 4B shows the implant being forced out of the delivery syringe 140 into the lens capsule. FIG. 4C shows unfolding of haptics wings 126 inside the lens capsule and FIG. 4D shows proper orientation of the implant, including fully deployed haptics wings 126, within the lens capsule.

Reference is now made to FIGS. 5 and 6, which are simplified pictorial and sectional illustrations of the injectable intraocular implant of FIGS. 1A-1D located in a specially designed, non fluid-filled hypodermic delivery syringe 160. It is seen that haptics wings 126 are folded over the optics portion 100 and that the implant is arranged with outward facing ends 110 and 130 arranged rearward in a delivery tube 162 of delivery syringe 160. A piston 166 of delivery syringe 160 engages outward facing end 110 of the optics portion 100 of the implant.

Reference is now made to FIGS. 7A, 7B, 7C and 7D, which are simplified sectional illustrations of four stages of the injection of the intraocular implant of FIGS. 1A-1D in the delivery syringe arrangement of FIGS. 5 & 6 into the eye of a patient. FIG. 7A shows initial insertion of the tip of the delivery tube 162 of delivery syringe 160 into the lens capsule of the eye. FIG. 7B shows the implant being forced out of the delivery syringe 160 into the lens capsule. FIG. 7C shows unfolding of haptics wings 126 inside the lens capsule and FIG. 7D shows proper orientation of the implant, including fully deployed haptics wings 126, within the lens capsule.

Reference is now made to FIGS. 8A-8D, which illustrate an injectable intraocular implant constructed and operative in accordance with another preferred embodiment of the present invention. It is seen that the implant preferably includes an optics portion 200 and a haptics portion 202 which is preferably snap-fitted onto the optics portion 200.

The optics portion 200 may be any suitable optics portion and is preferably, but not necessarily, a telescope. Preferred intraocular implants are described in applicants/assignee's published patent documents listed hereinbelow, the disclosures of which are hereby incorporated by reference:

U.S. Pat. Nos. 5,391,202; 5,354,335; 5,814,103; 5,876,442; 5,928,283; 6,007,579; 6,066,171; 6,569,199 and 6,596,026, and U.S. published applications U.S. Ser. Nos. 10/342,160 and 10/321,793.

The optics portion 200 may incorporate any one or more of the features described in the abovementioned patent documents in any suitable combination and is preferably in the form of a cylinder having adjacent one end thereof, hereinafter referred to as the inward facing end 210, a peripheral groove 212. The haptics portion 202 is preferably formed of a resilient, flexible material, such as biocompatible plastic, and includes a generally cylindrical optics engagement portion 220 integrally formed with an outwardly extending helical portion 222 and a generally cylindrical end portion 224.

Cylindrical optics engagement portion 220 is preferably formed with an inwardly directed peripheral protrusion 228 adjacent one end thereof, hereinafter referred to as the inward facing end 230. Protrusion 228 is arranged for normally non-removable snap-fit engagement with groove 212 on optics portion 200, when cylindrical optics engagement portion 220 is in coaxial surrounding relationship with optics portion 200 as shown.

It is appreciated that the peripheral groove 212 of the optics portion 200 may be located at any suitable location therealong and the inwardly directed peripheral protrusion 228 of cylindrical optics engagement portion 220 of haptics portion 202 may be located at any suitable location therealong to provide normally non-removable snap-fit engagement of optics portion 200 and haptics portion 202.

As seen in FIG. 8A, outwardly extending helical portion 222 preferably includes at least one, and preferably two or more, helical section 234 joined at one end to generally cylindrical optics engagement portion 220 and at an opposite end thereof to generally cylindrical end portion 224. Each of the at least one helical sections 234 preferably include a haptics spiral portion 236 connected to residual spiral portion 238 at a notched frangible portion 240. Notched frangible portions 240 provide for separation of haptics spiral portions 236 from residual spiral portion 238, as described hereinbelow with reference to FIG. 11B.

Alternatively, notched frangible portion 240 and residual spiral portion 238 may be obviated and haptics spiral portion 236 may be joined directly to generally cylindrical end portion 224. In this embodiment, end portion 224 is also injected into the lens capsule of an eye, as described hereinbelow with reference to FIGS. 12A-12D.

Figure 8C:
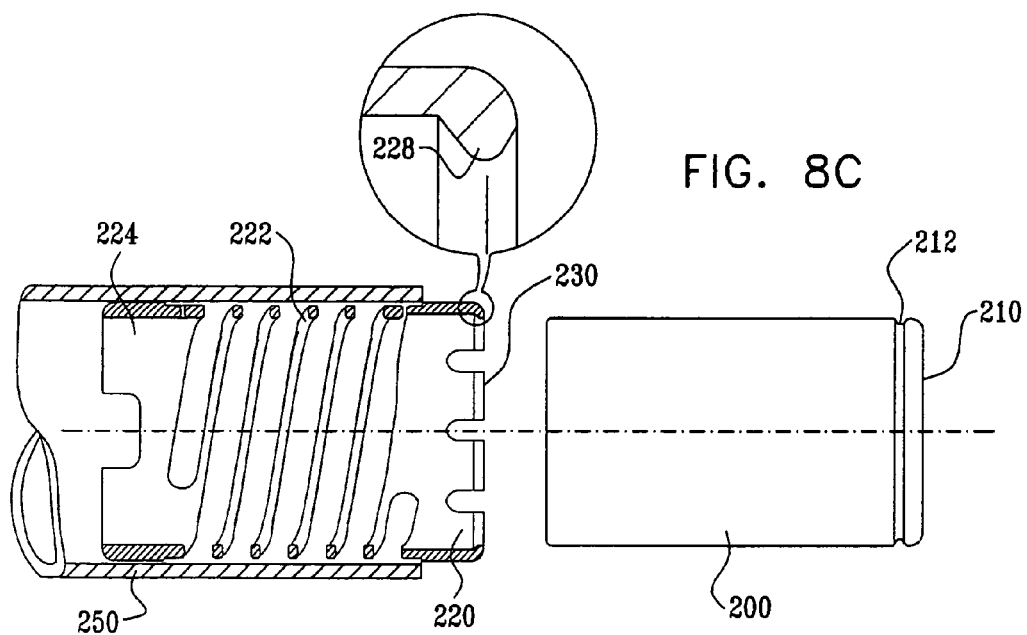
FIGS. 8C and 8D are simplified respective exploded and assembled side view illustrations of the injectable intraocular implant of FIGS. 8A & 8B.
Figure 8D:
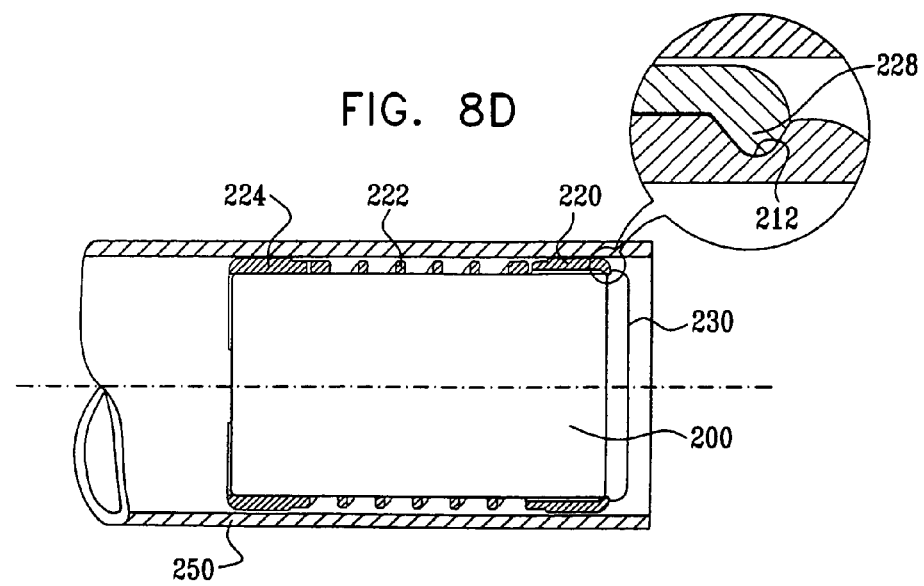

As seen further in FIGS. 8A, 8B and 8C, prior to injection of the intraocular implant of FIGS. 8A-8D into an eye, generally cylindrical end portion 224 is placed into a delivery syringe 250 and outwardly extending helical portion 222 is wound, as indicated by arrows 252 (FIG. 8A), into a tightly coiled position inside delivery syringe 250. As seen in FIG. 8D, cylindrical optics engagement portion 220 is then placed into snap fit engagement with optics portion 200.

Figure 9:
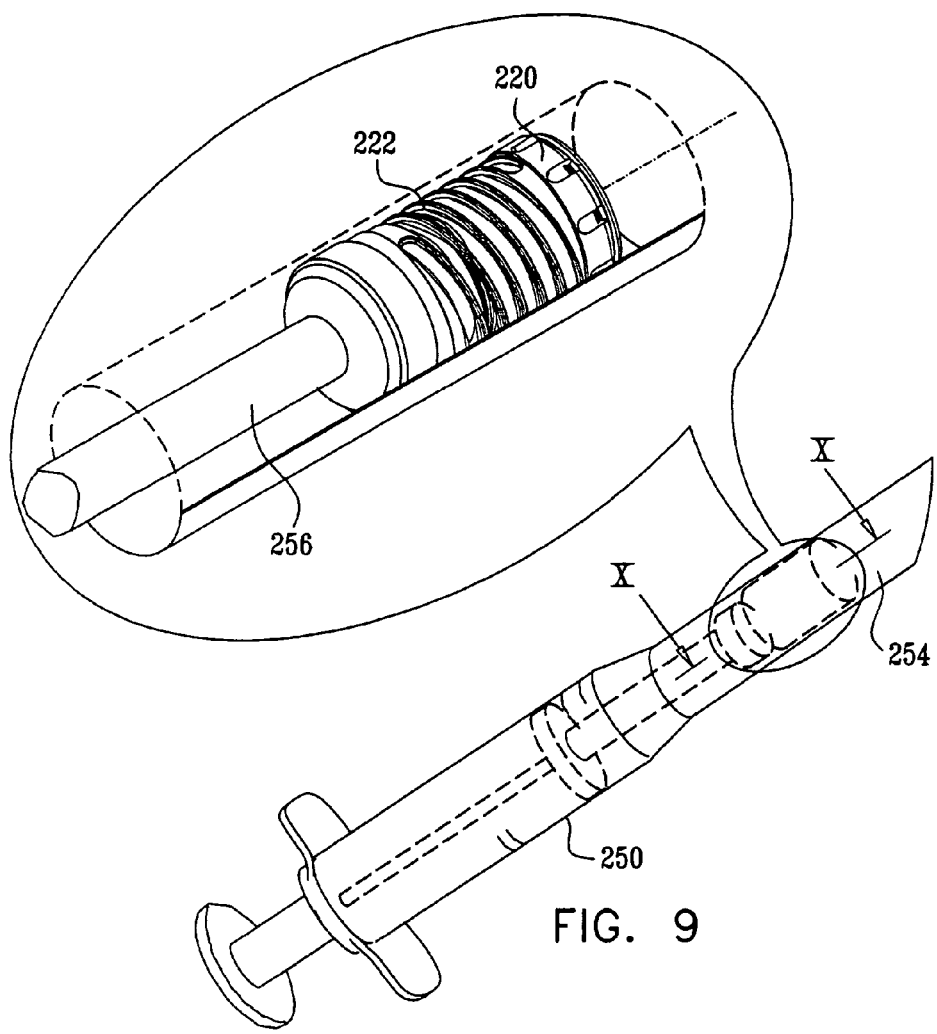
FIGS. 9 and 10 are simplified pictorial and sectional illustrations of the injectable intraocular implant of FIGS. 8A-8D located in a hypodermic delivery syringe.
Figure 10:
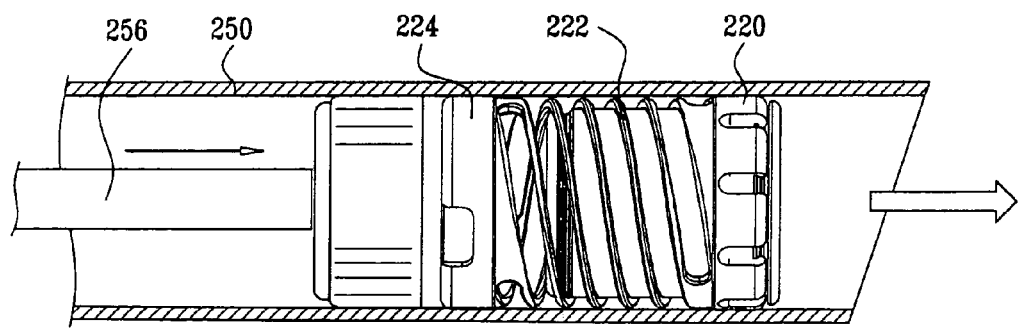

Reference is now made to FIGS. 9 and 10, which are simplified pictorial and sectional illustrations of the injectable intraocular implant of FIGS. 8A-8D located in delivery syringe 250. It is seen that outwardly extending helical portion 222 of haptics portion 202 is coiled over the optics portion 200 and that the implant is arranged with inward facing ends 210 and 230 arranged forwardly in a delivery tube 254 of delivery syringe 250. A piston 256 of delivery syringe 250 engages generally cylindrical end portion 224 of haptics portion 202.

Reference is now made to FIGS. 11A, 11B, 11C and 11D, which are simplified sectional illustrations of four stages of the injection of the intraocular implant of FIGS. 8A-8D in the delivery syringe arrangement of FIGS. 9 & 10 into the eye of a patient.

Figures 11A, 11B:
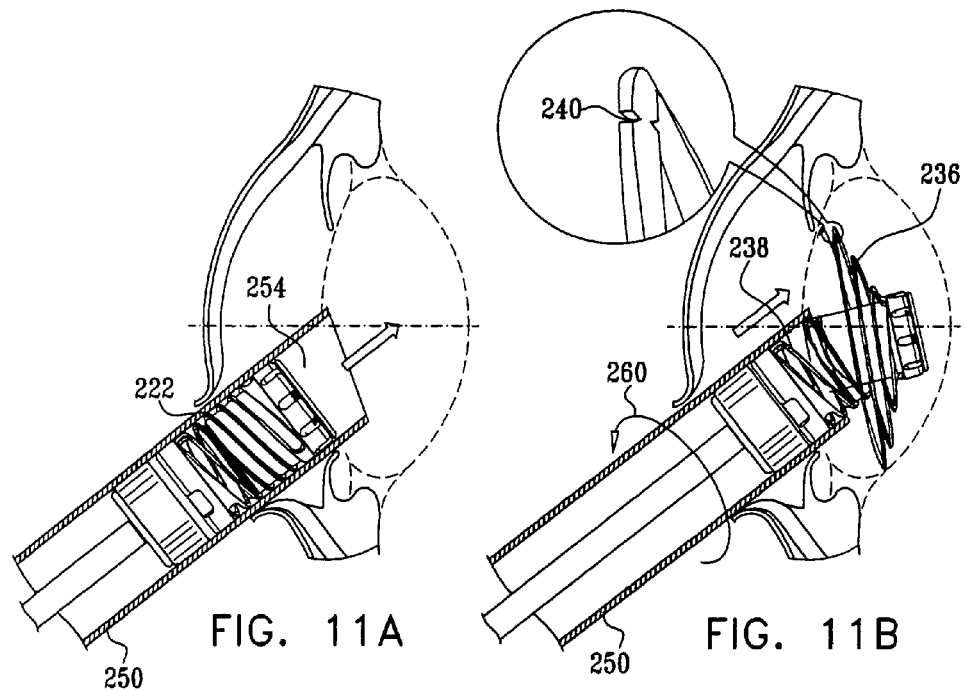
FIGS. 11A, 11B, 11C and 11D are simplified sectional illustrations of four stages of the injection of the intraocular implant of FIGS. 8A-8D in the delivery syringe arrangement of FIGS. 9 & 10 into the eye of a patient.

FIG. 11A shows initial insertion of the tip of the delivery tube 254 of delivery syringe 250 into the lens capsule of the eye.

FIG. 11B shows the implant being forced out of the delivery syringe 250 into the lens capsule. As seen in FIG. 11B, haptics spiral portion 236 uncoils and extends outwardly into the lens capsule upon exiting delivery syringe 250. Following the exiting of notched frangible portion 240 from delivery syringe 250, delivery syringe 250 is rotated, as designated by arrow 260, causing frangible portion 240 to break and separating haptics spiral portion 236 and residual spiral portion 238.

Figures 11C, 11D:
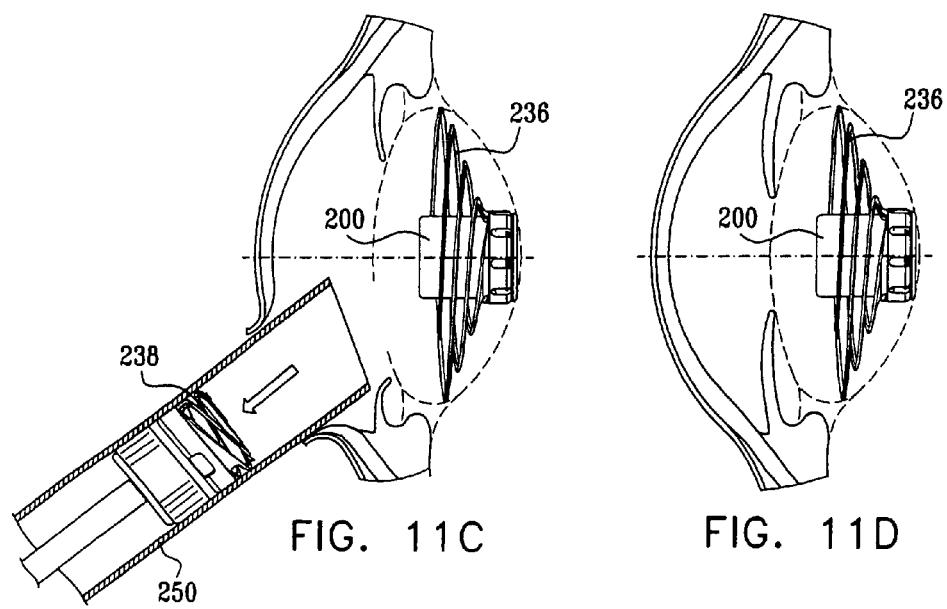

As seen in FIG. 11C, following the separation of haptics spiral portion 236 and residual spiral portion 238, haptics spiral portion 236 remains in the lens capsule together with optics portion 200, while residual spiral portion 238 remains within delivery syringe 250, which is then removed from the eye.

FIG. 11D shows proper orientation of the implant, including fully deployed haptics spiral portion 236 of haptics portion 202 and optics portion 200, within the lens capsule.

Reference is now made to FIGS. 12A, 12B, 12C and 12D, which are simplified sectional illustrations of four stages of the injection of the intraocular implant of FIGS. 8A-8D in the delivery syringe arrangement of FIGS. 9 & 10 into the eye of a patient in accordance with another preferred embodiment of the present invention. In the embodiment of FIGS. 12A-12D, haptics spiral portion 236 of the at least one helical section 234 is preferably joined at one end to generally cylindrical optics engagement portion 220 and at an opposite end thereof to generally cylindrical end portion 224, and helical section 234 preferably does not include a notched frangible portion 240 and residual spiral portion 238. Alternatively, helical section 234 may also include a notched frangible portion 240 and a residual spiral portion 238 joined to end portion 224.

FIG. 12A shows initial insertion of the tip of the delivery tube 254 of delivery syringe 250 into the lens capsule of the eye.

FIG. 12B shows the implant being forced out of the delivery syringe 250 into the lens capsule. As seen in FIG. 12B, haptics spiral portion 236 uncoils and extends outwardly into the lens capsule upon exiting delivery syringe 250. The embodiment of FIG. 12B differs from the embodiment of FIG. 11B in that delivery syringe 250 is not rotated to break notched frangible portion 240 and the entire haptics portion 202 is injected into the lens capsule.

As seen in FIGS. 12C-12D, following the injection of haptics portion 202 and optics portion 200, delivery syringe 250 is removed from the eye and outwardly extending helical portion 222 uncoils to its original form providing proper orientation of the implant, including fully deployed haptics spiral portion 236 of haptics portion 202 and optics portion 200, within the lens capsule.

Figure 13A:
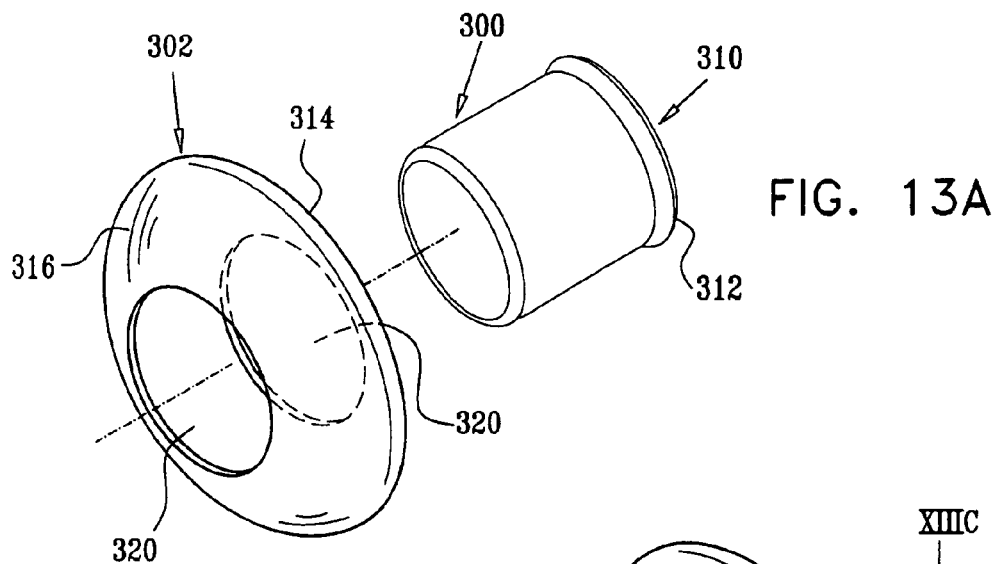
FIGS. 13A and 13B are simplified respective exploded and assembled pictorial illustrations of an injectable intraocular implant constructed and operative in accordance with yet another preferred embodiment of the present invention.
Figure 13B:
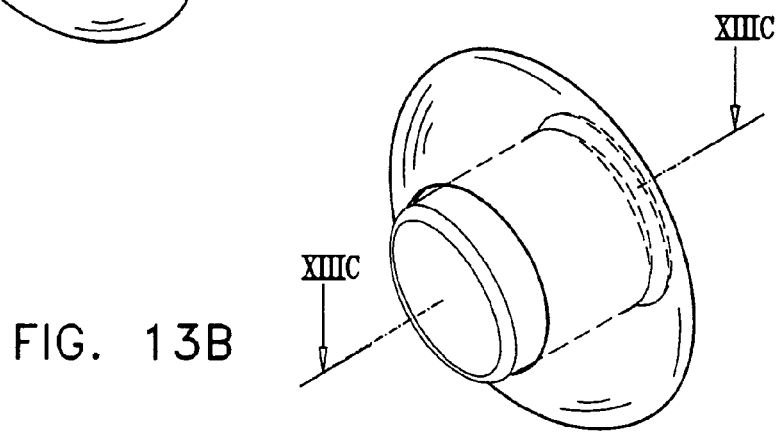
Figure 13C:
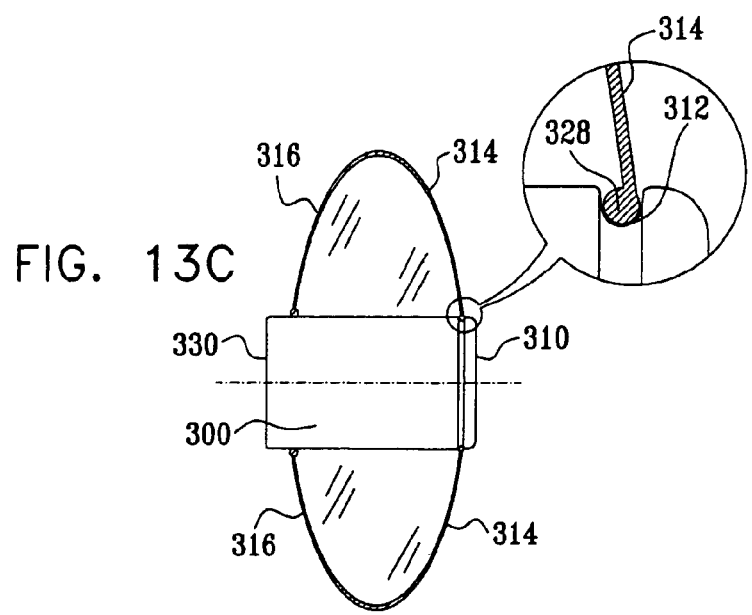
FIG. 13C is a simplified assembled side view illustration of the injectable intraocular implant of FIGS. 13A & 13B.

Reference is now made to FIGS. 13A-13C, which illustrate an injectable intraocular implant constructed and operative in accordance with yet another preferred embodiment of the present invention. It is seen that the implant preferably includes an optics portion 300 and a haptics portion 302 which is preferably snap-fitted onto the optics portion 300.

The optics portion 300 may be any suitable optics portion and is preferably, but not necessarily, a telescope. Preferred intraocular implants are described in applicants/assignee's published patent documents listed hereinbelow, the disclosures of which are hereby incorporated by reference:

U.S. Pat. Nos. 5,391,202; 5,354,335; 5,814,103; 5,876,442; 5,928,283; 6,007,579; 6,066,171; 6,569,199 and 6,596,026, and U.S. published applications U.S. Ser. Nos. 10/342,160 and 10/321,793.

The optics portion 300 may incorporate any one or more of the features described in the abovementioned patent documents in any suitable combination and is preferably in the form of a cylinder having adjacent one end thereof, hereinafter referred to as the inward facing end 310, a peripheral groove 312.

The haptics portion 302 is preferably formed of a resilient, flexible material, with a hollow, generally cylindrical structure defining a generally circular inward facing wall portion 314 and a generally circular outward facing wall portion 316. Each of wall portions 314 and 316 preferably define a generally circular optics engagement aperture 320 therein. Each of wall portions 314 and 316 is preferably formed with an inwardly directed peripheral protrusion 328 adjacent optics engagement aperture 320 thereof. Protrusion 328 of wall portion 314 is arranged for normally non-removable snap-fit engagement with groove 312 of optics portion 300, when haptics portion 302 is in coaxial surrounding relationship with optics portion 300 as shown.

Protrusion 328 of wall portion 316 is arranged for engagement of wall portion 316 with a delivery syringe as described further hereinbelow.

It is appreciated that while haptics portion 302 is preferably formed of a transparent material, it may be formed with non-transparent portions as suitable to eliminate and/or reduce glare.

Figure 14A:
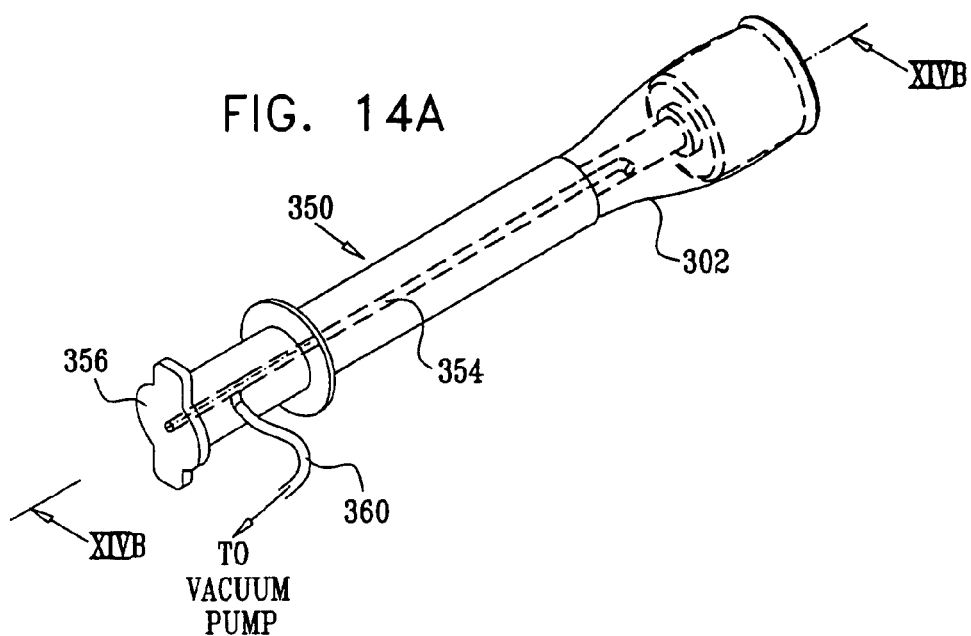
FIGS. 14A and 14B are simplified pictorial and sectional illustrations of the injectable intraocular implant of FIGS. 13A-13C located in a delivery syringe.
Figure 14B:
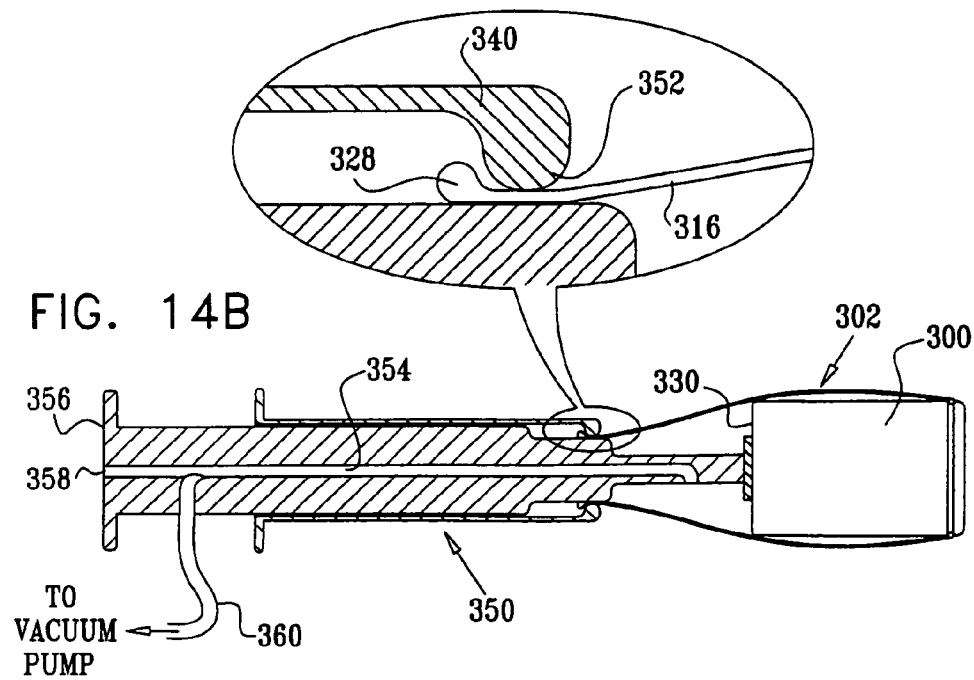

Reference is now made to FIGS. 14A and 14B, which are simplified pictorial and sectional illustrations of the injectable intraocular implant of FIGS. 13A-13C located in a delivery syringe and to FIGS. 15A, 15B, 15C and 15D, which are simplified sectional illustrations of four stages of the injection of the intraocular implant of FIGS. 13A-13C in the delivery syringe arrangement of FIGS. 14A & 14B into the eye of a patient.

As seen in FIGS. 14A-14B, prior to injection of the intraocular implant of FIGS. 13A-13C into an eye, outward facing wall portion 316 of haptics portion 302 is pulled over an outward facing end 330 of optics portion 300 and drawn into engagement with an outer wall 340 of a delivery syringe 350. As seen particularly in FIG. 14B, outer wall 340 preferably includes an inwardly directed peripheral protrusion 352 which engages protrusion 328 of wall portion 316 and thereby secures wall portion 316 of haptics portion 302 to delivery syringe 350. As seen further in FIGS. 14A-14B, the pulling of wall portion 316 causes haptics portion 302 to be temporarily deformed into an elongated generally cylindrical orientation overlying optics portion 300.

Delivery syringe 350 preferably also includes a fluid flow passageway 354 in fluid communication with a rearward facing wall 356 of syringe 350 at a location 358. Fluid flow passageway 354 is also preferably in fluid communication with a vacuum pump (not shown) via a tube 360.

As seen in FIG. 15A, prior to insertion of the injectable intraocular implant into the lens capsule, fluid flow passageway 354 is temporarily sealed by covering location 358, and the vacuum pump is operated to remove air contained within haptics portion 302. FIG. 15A shows initial insertion of delivery syringe 350 into the lens capsule of the eye. It is appreciated that the operation of the vacuum pump allows haptics portion 302 to closely overly optics portion 300.

Figure 15C:
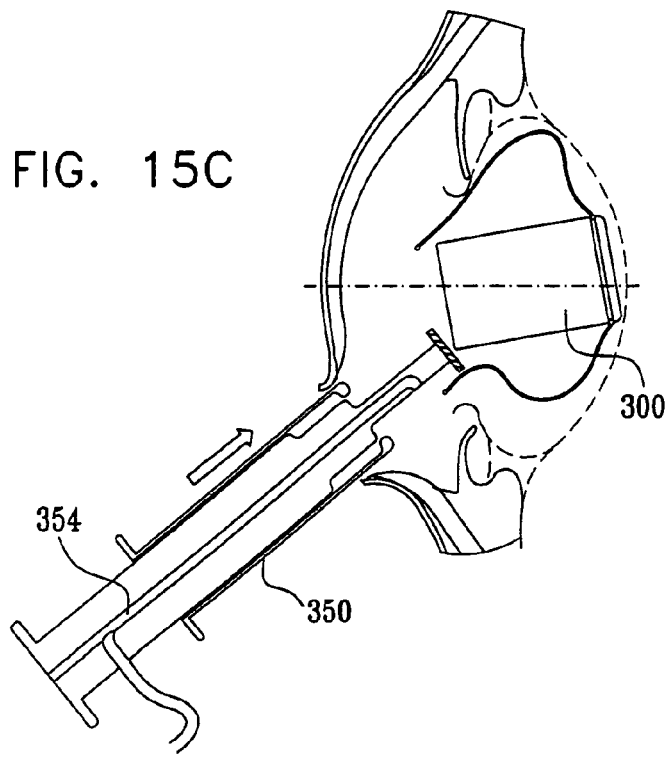

As seen further in FIGS. 15B-15C, following placement of the implant into the lens capsule, haptics portion 302 of the implant expands outwardly from the optics portion 300 as wall portions 314 and 316 of haptics portion 302 return to their original generally circular orientation. As seen in FIG. 15B, the unsealing of fluid flow passageway 354 allows air to flow therethrough and into the space formed between haptics portion 302 and optics portion 300, causing expansion of haptics portion 302 and causing outer wall 340 of delivery syringe 350 to disengage from protrusion 328 of wall portion 316 of haptics portion 302.

Figure 15D:
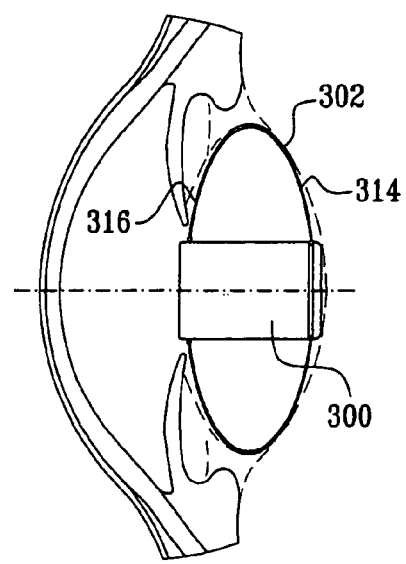

As seen in FIG. 15D, following the injection of haptics portion 302 and optics portion 300, delivery syringe 350 is removed from the eye and haptics portion 302 returns to its original form providing proper orientation of the implant, including fully deployed haptics portion 302 and optics portion 300, within the lens capsule.

Reference is now made to FIGS. 16A-16C, which illustrate an injectable intraocular implant constructed and operative in accordance with yet another preferred embodiment of the present invention. It is seen that the implant preferably includes an optics portion 400 and a haptics portion 402 which is preferably snap-fitted or shrink-fitted onto the optics portion 400.

The optics portion 400 may be any suitable optics portion and is preferably, but not necessarily, a telescope. Preferred intraocular implants are described in applicants/assignee's published patent documents listed hereinbelow, the disclosures of which are hereby incorporated by reference:

U.S. Pat. Nos. 5,391,202; 5,354,335; 5,814,103; 5,876,442; 5,928,283; 6,007,579; 6,066,171; 6,569,199 and 6,596,026, and U.S. published applications U.S. Ser. Nos. 10/342,160 and 10/321,793.

The optics portion 400 may incorporate any one or more of the features described in the abovementioned patent documents in any suitable combination and is preferably in the form of a cylinder having adjacent one end thereof, hereinafter referred to as the inward facing end 410, a peripheral groove 412.

The haptics portion 402 is preferably formed of a resilient, flexible material, with a hollow, generally cylindrical structure defining a generally circular inward facing wall portion 414 and a generally circular outward facing wall portion 416. Wall portion 414 preferably defines a generally circular optics engagement aperture 420 therein. Wall portion 414 is preferably formed with an inwardly directed peripheral protrusion 428 adjacent optics engagement aperture 420. Protrusion 428 of wall portion 414 is arranged for normally non-removable snap-fit or tension-fit engagement with groove 412 of optics portion 400, when haptics portion 402 is in coaxial surrounding relationship with optics portion 400 as shown.

It is appreciated that while haptics portion 402 is preferably formed of a transparent material, it may be formed with non-transparent portions as suitable to eliminate and/or reduce glare.

Figure 17A:
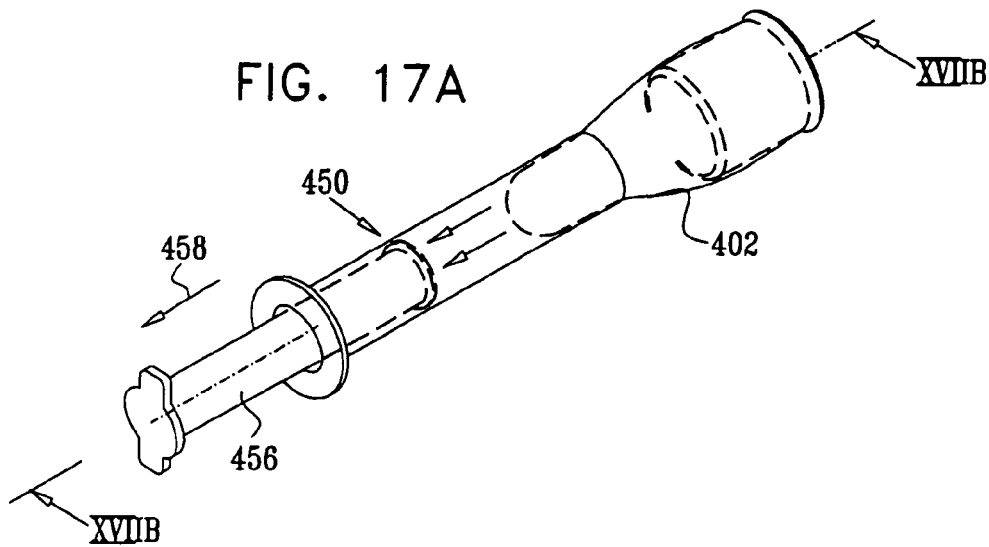
FIGS. 17A and 17B are simplified pictorial and sectional illustrations of the injectable intraocular implant of FIGS. 16A-16C located in a delivery syringe.
Figure 17B:
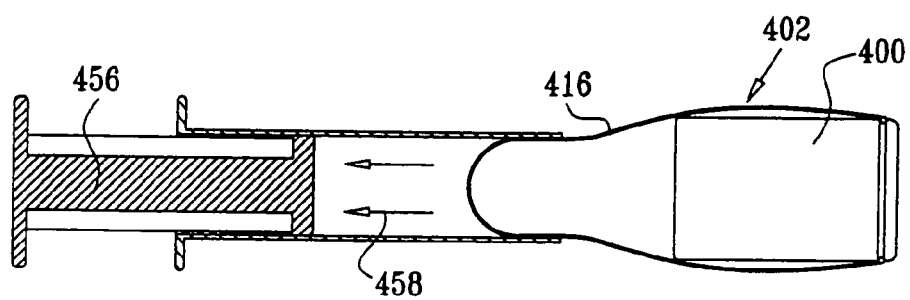

Reference is now made to FIGS. 17A and 17B, which are simplified pictorial and sectional illustrations of the injectable intraocular implant of FIGS. 16A-16C located in a delivery syringe and to FIGS. 18A, 18B, 18C and 18D, which are simplified sectional illustrations of four stages of the injection of the intraocular implant of FIGS. 16A-16C in the delivery syringe arrangement of FIGS. 17A & 17B into the eye of a patient.

As seen in FIGS. 17A-17B, prior to injection of the intraocular implant of FIGS. 16A-16C into an eye, outward facing wall portion 416 of haptics portion 402 is drawn into a vacuum delivery syringe 450 by extending a plunger 456 in the direction of arrow 458. As seen in FIGS. 17A-17B, the drawing of wall portion 416 into delivery syringe 450 causes haptics portion 402 to be temporarily deformed into an elongated generally cylindrical orientation overlying optics portion 400.

Figure 18A:
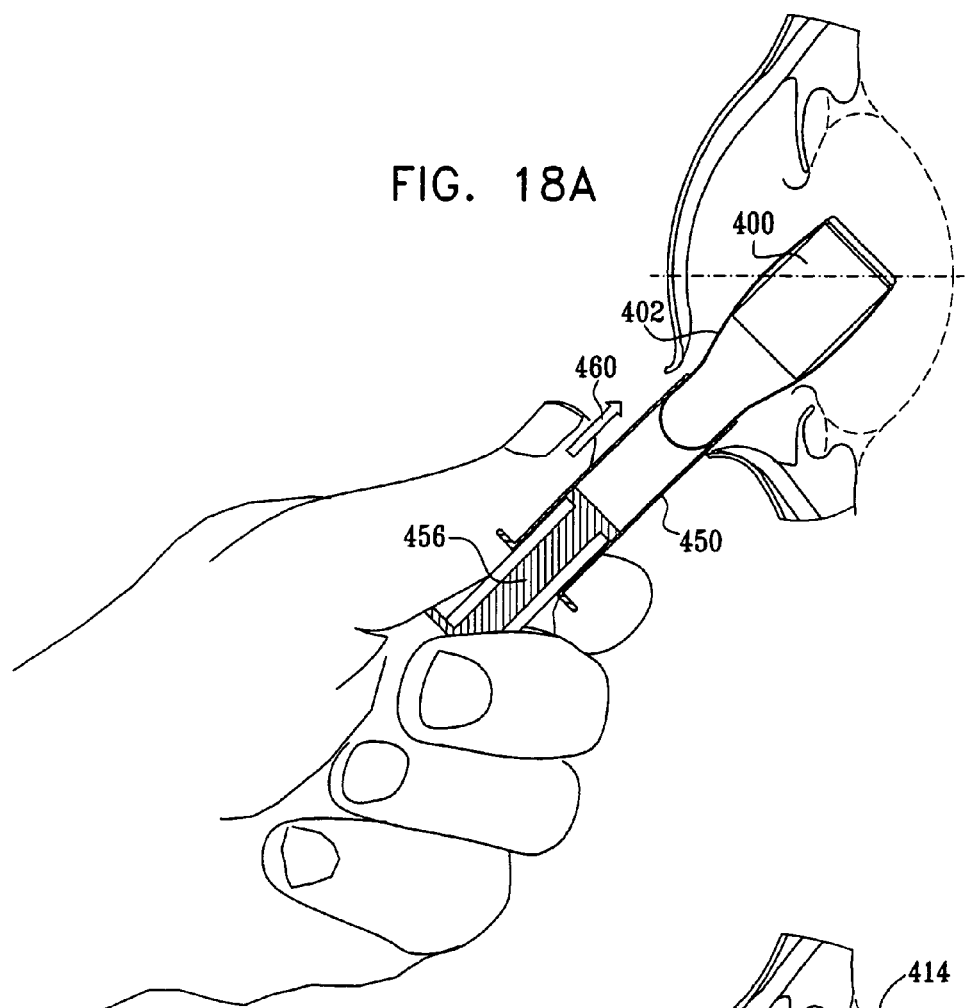
FIGS. 18A, 18B, 18C and 18D are simplified sectional illustrations of four stages of the injection of the intraocular implant of FIGS. 16A-16C in the delivery syringe arrangement of FIGS. 17A & 17B into the eye of a patient.

FIG. 18A shows initial insertion of delivery syringe 450 into the lens capsule of the eye, in the direction of arrow 460. It is appreciated that maintaining plunger 456 in the position of FIGS. 17A-17B maintains the vacuum inside delivery syringe 450 and allows haptics portion 402 to closely overly optics portion 400 during initial insertion of syringe 450 into the lens capsule.

Figure 18B:
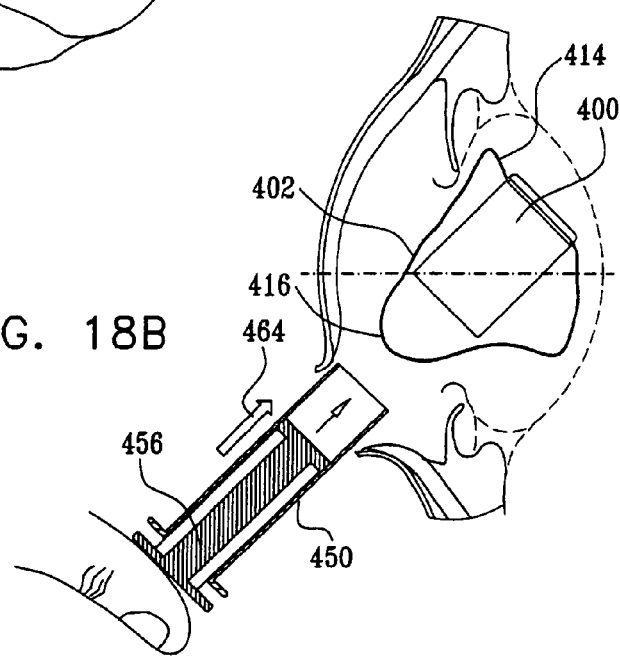

As seen further in FIG. 18B, following placement of the implant into the lens capsule, plunger 456 is pushed in the direction of arrow 464 and haptics portion 402 of the implant is released from syringe 450. Following release of the implant from delivery syringe 450, haptics portion 402 expands outwardly from the optics portion 400 as wall portions 414 and 416 of haptics portion 402 return to their original generally circular orientation.

Figures 18C, 18D:
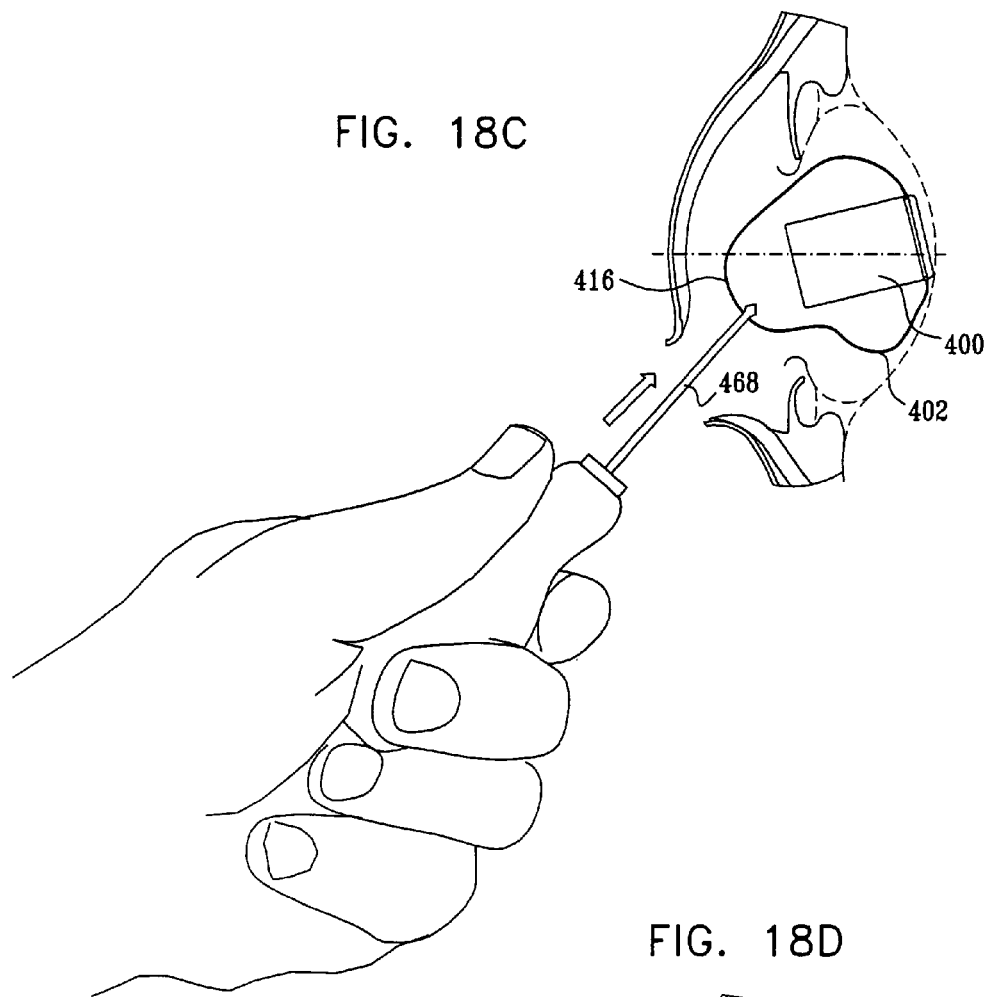

As seen further in FIG. 18C, following release of the implant and removal of delivery syringe 450, an aperture is made in wall portion 416, preferably through puncturing wall portion 416 with a hook 468, to allow aqueous fluid from the eye to flow into the area between optics portion 400 and haptics portion 402. As seen further in FIG. 18D, following the removal of hook 468, haptics portion 402 fills with aqueous fluid 470 and returns to its original form providing proper orientation of the implant, including fully deployed haptics portion 402 and optics portion 400, within the lens capsule.

Figure 19A:
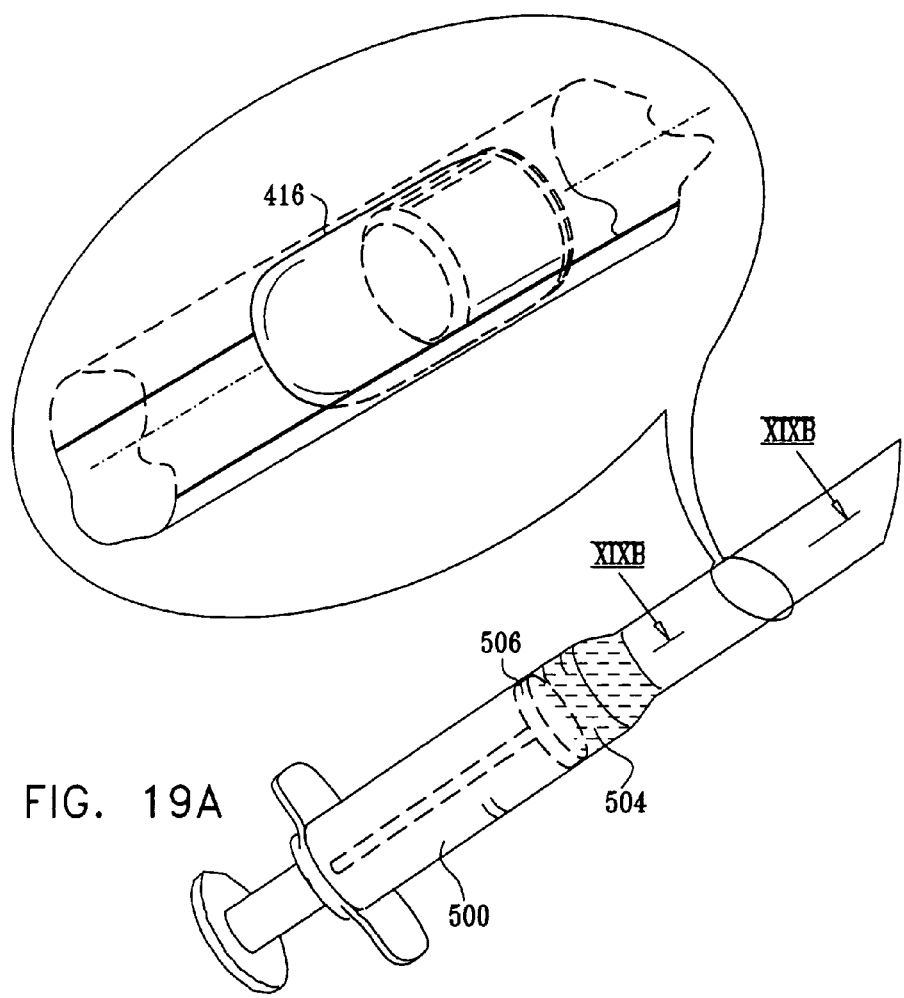
FIGS. 19A and 19B are simplified pictorial and sectional illustrations of the injectable intraocular implant of FIGS. 16A-16C located in a delivery syringe.
Figure 19B:
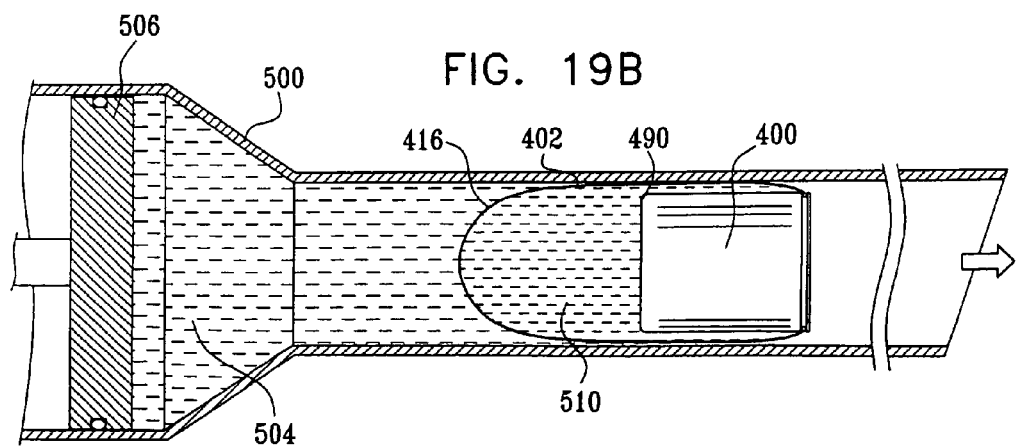

Reference is now made to FIGS. 19A and 19B, which are simplified pictorial and sectional illustrations of the injectable intraocular implant of FIGS. 16A-16C located in a fluid-filled delivery syringe and to FIGS. 20A, 20B, 20C and 20D, which are simplified sectional illustrations of four stages of the injection of the intraocular implant of FIGS. 16A-16C in the delivery syringe arrangement of FIGS. 19A & 19B into the eye of a patient.

As seen in FIGS. 19A-19B, prior to injection of the intraocular implant of FIGS. 16A-16C into an eye, outward facing wall portion 416 of haptics portion 402 is pulled over an outward facing end 490 of optics portion 400 and the intraocular implant is inserted into a fluid-filled delivery syringe 500. As seen in FIGS. 19A-19B, the pulling of wall portion 416 over end 490 causes haptics portion 402 to be temporarily deformed into an elongated generally cylindrical orientation overlying optics portion 400. Fluid, such as biocompatible fluid 504, is located forward of a piston 506 of delivery syringe 500 and rearward of the implant.

It is appreciated that haptics portion 402 may be filled, using any suitable method, with any suitable biocompatible fluid 510, such as saline or air, prior to insertion into delivery syringe 500. It is further appreciated that insertion of fluid 510 into haptics portion 402 provides cushioning for the intraocular implant during the injection thereof into an eye.

Figure 20A:
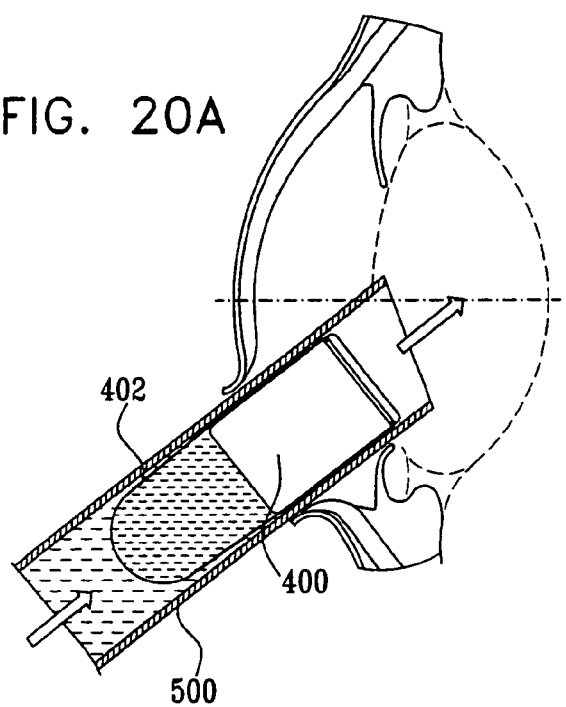
FIGS. 20A, 20B, 20C and 20D are simplified sectional illustrations of four stages of the injection of the intraocular implant of FIGS. 16A-16C in the delivery syringe arrangement of FIGS. 19A & 19B into the eye of a patient.

FIG. 20A shows initial insertion of the tip of delivery syringe 500 into the lens capsule of the eye. It is appreciated that the temporary deforming of haptics portion 402 allows haptics portion 402 to closely overly optics portion 400 inside syringe 500.

Figure 20B:
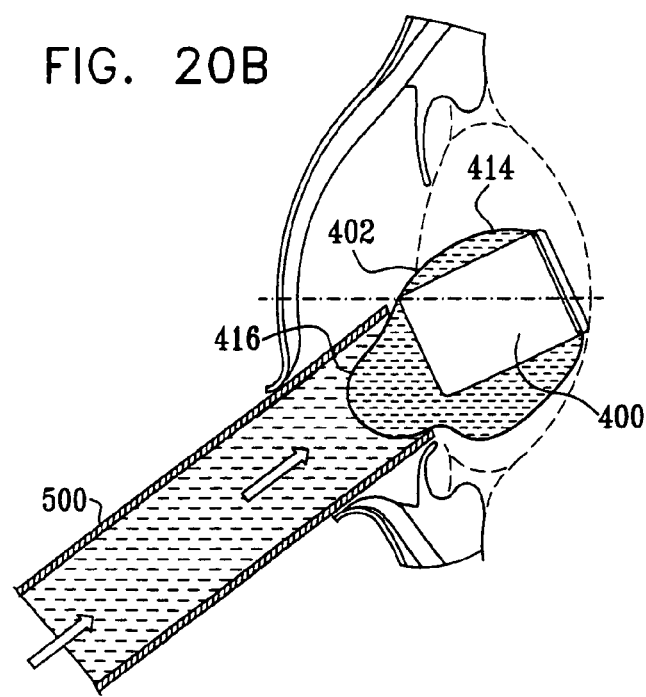

As seen further in FIG. 20B, following placement of the delivery syringe 500 into the lens capsule, the implant is forced out of the syringe 500 into the lens capsule. As seen in FIG. 20B, haptics portion 402 expands outwardly from the optics portion 400 as wall portions 414 and 416 of haptics portion 402 return to their generally circular orientation. Syringe 500 is subsequently removed from the lens capsule.

Figures 20C, 20D:
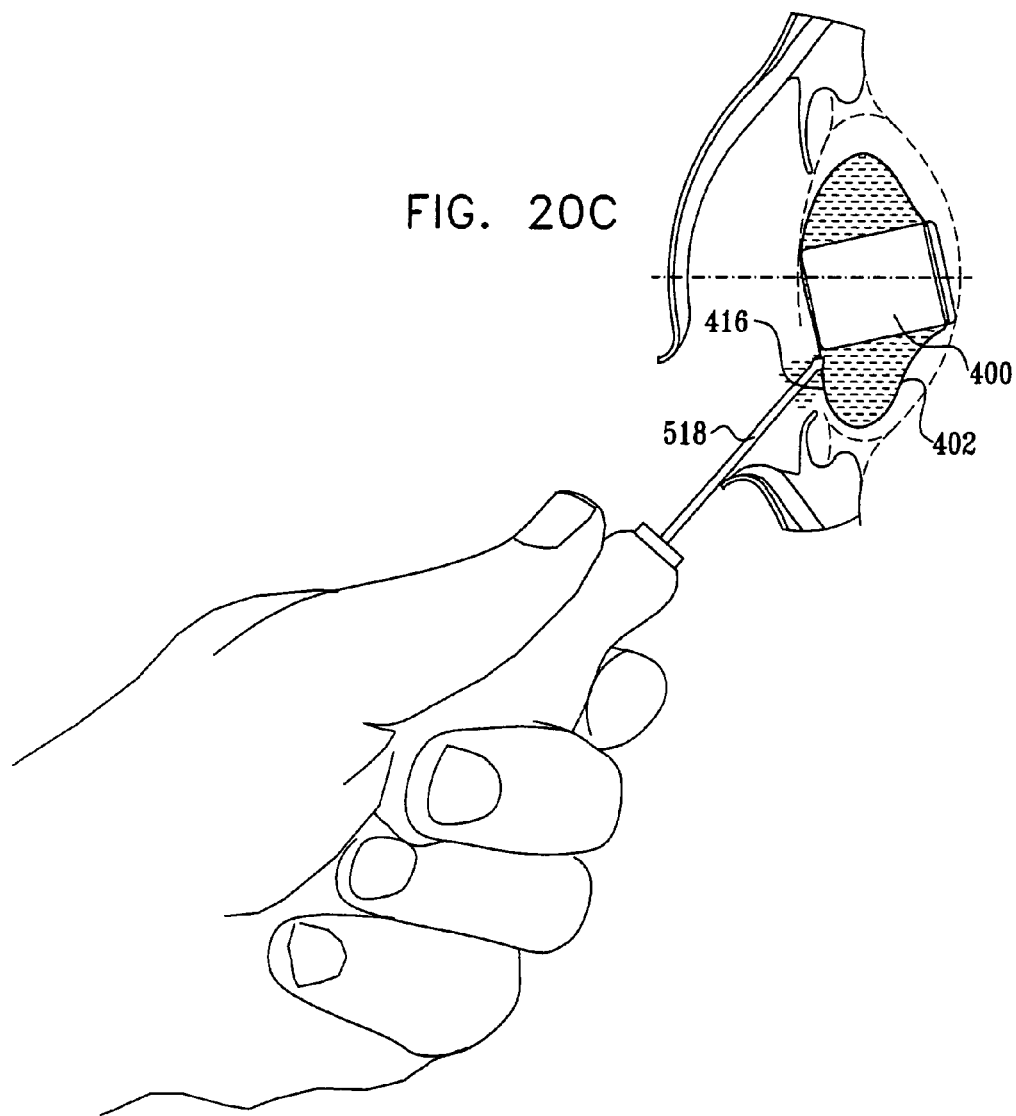

As seen further in FIG. 20C, an aperture is made in wall portion 416, preferably through puncturing wall portion 416 with a hook 518, to allow aqueous fluid from the eye to flow into the area between optics portion 400 and haptics portion 402 and mix with biocompatible fluid 510. Alternatively, haptics portion 402 is not filled with biocompatible fluid 510 prior to insertion into delivery syringe 500 and the puncturing of wall portion 416 allows aqueous fluid from the eye to flow into the area between optics portion 400 and haptics portion 402.

As seen further in FIG. 20D, following the removal of hook 518, haptics portion 402 returns to its original form providing proper orientation of the implant, including fully deployed haptics portion 402 and optics portion 400, within the lens capsule.

It will be appreciated by persons skilled in the art that the present invention is not limited to what has been particularly shown and described hereinabove. Rather the scope of the present invention includes both combinations and subcombinations of features described hereinabove as well as variations and modifications thereof which would occur to a person skilled in the art upon reading the foregoing description, taken together with the drawings, and which are not in the prior art.

The invention claimed is:

1. An injectable intraocular implant comprising:
   an optics portion arranged along an optical axis; and
   a separate resilient, flexible haptics portion configured for coaxial engagement with said optics portion;
   said haptics portion including a ring portion having integrally formed therewith a plurality of haptics wings, each of said plurality of haptics wings including a pair of side peripheral edges joined by an outer peripheral edge, said peripheral edges circumscribing a haptics wing area,
   said plurality of haptics wings having a post-implantation operative orientation, wherein said haptics wing areas of said plurality of haptics wings lie generally transverse to said optical axis, and a pre-implantation operative orientation, wherein said haptics wing areas of said plurality of haptics wings lie generally parallel to said optical axis,
   said plurality of haptics wings being adapted to automatically unfold from said pre-implantation operative orientation to assume said post-implantation operative orientation by pivoting of said side peripheral edges about pivot axes which are tangential to the circumference of said ring portion.

2. An injectable intraocular implant according to claim 1 and wherein said optics portion and said haptics portion are arranged for mutual snap fit engagement.

3. An injectable intraocular implant according to claim 1 and wherein said optics portion comprises a telescope.

4. An injectable intraocular implant according to claim 1 and wherein said haptics portion is formed of biocompatible plastic.

5. An injectable intraocular implant according to claim 1 and wherein said ring portion is in coaxial surrounding relationship with said optics portion.

6. An injectable intraocular implant according to claim 1 and wherein said outer peripheral edges of said haptics wings are adapted to engage a lens capsule of an eye.

* * * * *